United States Patent
Gee et al.

(10) Patent No.: US 9,708,549 B2
(45) Date of Patent: Jul. 18, 2017

(54) METHOD FOR MAKING POLYALPHAOLEFINS USING ALUMINUM HALIDE CATALYZED OLIGOMERIZATION OF OLEFINS

(71) Applicant: Chevron Phillips Chemical Company LP, The Woodlands, TX (US)

(72) Inventors: Jeffery C. Gee, Kingwood, TX (US); Brooke L. Small, Kingwood, TX (US); Kenneth D. Hope, Kingwood, TX (US); Robert C. Coffin, Kingwood, TX (US); Steven M. Bischof, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 724 days.

(21) Appl. No.: 14/132,208

(22) Filed: Dec. 18, 2013

(65) Prior Publication Data

US 2015/0166429 A1 Jun. 18, 2015

(51) Int. Cl.
| | | |
|---|---|---|
| *C07C 2/24* | (2006.01) | |
| *C07C 9/00* | (2006.01) | |
| *C07C 11/02* | (2006.01) | |
| *C07C 5/05* | (2006.01) | |
| *C10G 50/02* | (2006.01) | |
| *C07C 2/22* | (2006.01) | |
| *C10G 50/00* | (2006.01) | |
| *C10G 69/12* | (2006.01) | |

(52) U.S. Cl.
CPC ................ *C10G 50/02* (2013.01); *C07C 2/22* (2013.01); *C10G 50/00* (2013.01); *C10G 69/126* (2013.01); *C07C 2527/125* (2013.01); *C07C 2527/126* (2013.01); *C10G 2300/1088* (2013.01); *C10G 2400/10* (2013.01); *C10G 2400/22* (2013.01)

(58) Field of Classification Search
CPC ................ C07C 2/22; C07C 2527/126; C07C 2527/125; C10G 50/02; C10G 69/126; C10G 50/00; C10G 2300/1088; C10G 2400/10; C10G 2400/22
See application file for complete search history.

(56) References Cited

U.S. PATENT DOCUMENTS

| | | |
|---|---|---|
| 1,815,022 A | 7/1931 | Davis |
| 2,015,748 A | 10/1935 | Frolich |
| 2,191,498 A | 2/1940 | Reiff |
| 2,387,501 A | 10/1945 | Dietrich |
| 2,443,264 A | 6/1948 | Mikeska |
| 2,471,115 A | 5/1949 | Mikeska |
| 2,526,497 A | 10/1950 | Mikeska |
| 2,559,984 A | 7/1951 | Montgomery et al. |
| 2,591,577 A | 4/1952 | McDermott |
| 2,655,479 A | 10/1953 | Munday et al. |
| 2,666,746 A | 1/1954 | Munday et al. |
| 2,719,125 A | 9/1955 | Roberts |
| 2,719,126 A | 9/1955 | Fields et al. |
| 2,721,877 A | 10/1955 | Popkin et al. |
| 2,721,878 A | 10/1955 | Popkin |
| 2,830,977 A * | 4/1958 | Ernst .................. C08F 36/04 526/237 |
| 3,036,003 A | 5/1962 | Verdol |
| 3,087,932 A | 4/1963 | Little, Jr. |
| 3,087,936 A | 4/1963 | Le Suer |
| 3,149,178 A | 9/1964 | Hamilton et al. |
| 3,172,892 A | 3/1965 | Le Suer et al. |
| 3,200,107 A | 8/1965 | Le Suer |
| 3,215,707 A | 11/1965 | Rense |
| 3,219,666 A | 11/1965 | Norman et al. |
| 3,250,715 A | 5/1966 | Wyman |
| 3,254,025 A | 5/1966 | Le Suer |
| 3,272,746 A | 9/1966 | Le Suer et al. |
| 3,275,554 A | 9/1966 | Wagenaar |
| 3,316,177 A | 4/1967 | Dorer, Jr. |
| 3,322,670 A | 5/1967 | Burt et al. |
| 3,329,658 A | 7/1967 | Fields |
| 3,330,883 A | 7/1967 | Giannetti et al. |

(Continued)

OTHER PUBLICATIONS

UCalgary, http://www.chem.ucalgary.ca/courses/350/orgnom/alkenes/alkenes-02.html, accessed Jan. 21, 2017.*

(Continued)

*Primary Examiner* — In Suk Bullock
*Assistant Examiner* — Ali Z Fadhel
(74) *Attorney, Agent, or Firm* — Conley Rose, P.C.; Rodney B. Carroll; Lynda Jolly

(57) ABSTRACT

The present application relates to method for oligomerizing olefin or for producing polyalphaolefin utilizing catalyst mixtures comprising aluminum halides and an organic liquid carrier. A process comprising contacting 1) a catalyst mixture comprising i) an aluminum trihalide and ii) an organic liquid carrier comprising first olefins, wherein the organic liquid carrier first olefins comprise at least 60 mole % 1,2-disubstituted olefins, trisubstituted olefins, or any combination thereof; and 2) a monomer comprising second olefins to form an oligomer product. An oligomer product produced by the process comprising contacting 1) a catalyst mixture comprising i) an aluminum trihalide and ii) an organic liquid carrier comprising first olefins, wherein the organic liquid carrier olefins comprise at least 75 mole % 1,2-disubstituted olefins, trisubstituted olefins, or any combination thereof; and 2) a monomer comprising second olefins to form an oligomer product.

21 Claims, No Drawings

(56) References Cited

U.S. PATENT DOCUMENTS

| | | | |
|---|---|---|---|
| 3,341,542 A | 9/1967 | Le Suer et al. | |
| 3,413,347 A | 11/1968 | Worrel | |
| 3,438,757 A | 4/1969 | Honnen et al. | |
| 3,444,170 A | 5/1969 | Norman et al. | |
| 3,449,250 A | 6/1969 | Fields | |
| 3,454,555 A | 7/1969 | van der Voort et al. | |
| 3,454,607 A | 7/1969 | Le Suer et al. | |
| 3,519,565 A | 7/1970 | Coleman | |
| 3,541,012 A | 11/1970 | Stuebe | |
| 3,565,804 A | 2/1971 | Honnen et al. | |
| 3,630,904 A | 12/1971 | Musser et al. | |
| 3,632,511 A | 1/1972 | Liao | |
| 3,637,503 A | 1/1972 | Giannetti et al. | |
| 3,652,616 A | 3/1972 | Watson et al. | |
| 3,666,730 A | 5/1972 | Coleman | |
| 3,687,849 A | 8/1972 | Abbott | |
| 3,697,574 A | 10/1972 | Piasek et al. | |
| 3,702,300 A | 11/1972 | Coleman | |
| 3,703,536 A | 11/1972 | Piasek et al. | |
| 3,704,308 A | 11/1972 | Piasek et al. | |
| 3,725,277 A | 4/1973 | Worrel | |
| 3,725,480 A | 4/1973 | Traise et al. | |
| 3,725,498 A * | 4/1973 | Brennan | B01J 27/125 502/169 |
| 3,726,882 A | 4/1973 | Traise et al. | |
| 3,749,560 A | 7/1973 | Perilstein | |
| 3,751,365 A | 8/1973 | Piasek et al. | |
| 3,755,433 A | 8/1973 | Miller et al. | |
| 3,756,953 A | 9/1973 | Piasek et al. | |
| 3,770,854 A | 11/1973 | Morris et al. | |
| 3,787,374 A | 1/1974 | Adams | |
| 3,798,165 A | 3/1974 | Piasek et al. | |
| 3,803,039 A | 4/1974 | Piasek et al. | |
| 3,822,209 A | 7/1974 | Knapp et al. | |
| 3,833,678 A | 9/1974 | Brennan | |
| 3,940,452 A | 2/1976 | Strassberger | |
| 3,948,800 A | 4/1976 | Meinhardt | |
| 3,954,897 A | 5/1976 | Yamato et al. | |
| 4,031,159 A | 6/1977 | Mandai et al. | |
| 4,100,082 A | 7/1978 | Clason et al. | |
| 4,167,534 A | 9/1979 | Petrillo et al. | |
| 4,214,111 A * | 7/1980 | Kitamura | C07C 2/22 585/255 |
| 4,234,435 A | 11/1980 | Meinhardt et al. | |
| 4,426,305 A | 1/1984 | Malec | |
| 4,434,308 A | 2/1984 | Larkin et al. | |
| 4,454,059 A | 6/1984 | Pindar et al. | |
| 4,469,912 A | 9/1984 | Blewett et al. | |
| 4,501,678 A | 2/1985 | Katayama et al. | |
| 4,658,078 A | 4/1987 | Slaugh et al. | |
| 4,697,040 A | 9/1987 | Williamson et al. | |
| 4,767,551 A | 8/1988 | Hunt et al. | |
| 4,798,684 A | 1/1989 | Salomon | |
| 4,906,798 A | 3/1990 | Lin | |
| 4,941,984 A | 7/1990 | Chamberlin, III et al. | |
| 4,973,788 A * | 11/1990 | Lin | C07C 2/30 585/511 |
| 5,034,141 A | 7/1991 | Beltzer et al. | |
| 5,034,142 A | 7/1991 | Habeeb et al. | |
| 5,082,956 A | 1/1992 | Monnier et al. | |
| 5,084,197 A | 1/1992 | Galic et al. | |
| 5,087,788 A | 2/1992 | Wu | |
| 5,196,635 A | 3/1993 | Kumar et al. | |
| 5,284,988 A * | 2/1994 | Schaerl, Jr. | C10G 50/02 585/16 |
| 5,451,704 A | 9/1995 | Ho et al. | |
| 5,573,657 A | 11/1996 | Degnan et al. | |
| 5,693,598 A | 12/1997 | Abraham et al. | |
| 5,705,458 A | 1/1998 | Roby et al. | |
| 6,002,060 A * | 12/1999 | Sarin | C07C 2/30 585/520 |
| 6,096,678 A | 8/2000 | Ray et al. | |
| 6,407,302 B1 | 6/2002 | Twu et al. | |
| 6,548,723 B2 | 4/2003 | Bagheri et al. | |
| 6,639,118 B1 | 10/2003 | McKinnie et al. | |
| 7,078,579 B2 | 7/2006 | Doll et al. | |
| 7,547,811 B2 | 6/2009 | Kramer et al. | |
| 7,550,640 B2 | 6/2009 | Surana et al. | |
| 7,989,670 B2 | 8/2011 | Wu et al. | |
| 8,178,050 B2 * | 5/2012 | Michielin | B01J 8/0045 406/124 |
| 8,207,390 B2 | 6/2012 | Wu et al. | |
| 2008/0146469 A1 | 6/2008 | Sato et al. | |
| 2009/0156874 A1 | 6/2009 | Patil et al. | |
| 2009/0240012 A1 | 9/2009 | Patil et al. | |
| 2010/0317904 A1 | 12/2010 | Small et al. | |
| 2013/0253244 A1 | 9/2013 | Emett et al. | |

OTHER PUBLICATIONS

International Application PCT/US2014/070875 Search Report dated Mar. 4, 2015.
"Group notation revised in periodic table," Feb. 4, 1985, pp. 26-27, C&EN.
Rudnick, Leslie R., et al., "Synthetic Lubricants and High-Performance Functional Fluids," 1999, 1 page, Second Edition, CRC Press.
Mang, Theo, et al., "Lubricants and Lubrication," 2001, 1 page, Wiley-VCH.
Totten, George E., "Fuels and Lubricants Handbook: Technology, Properties, Performance, and Testing," 2003, 3 pages, ASTM International.
Klamann, Dieter. "Lubricants and Related Products," 1984, pp. 199-248 plus 1 cover page, Verlag Chemie.
McNaught, Alan D., et al., "Compendium of Chemical Terminology," International Union of Pure and Applied Chemistry, Second edition, 1997, 5 pages of cover, publishing information, and contents, Wiley-Blackwell.
Ranney, M. W., "Lubricant Additives," Chemical Technology Review No. 2, 1973, 352 pages, Noyes Data Corporation.
Smalheer, C. V., et al., "Lubricant Additives," 1967, 91 pages, The Lezius-Hiles Co., The Lubrizol Corporation.
Sequeira, Jr., Avilino, "Lubricant Base Oil and Wax Processing," Chapter 6, "Lubricant Base Oil Hydrogen Refining Processes," pp. 119-152 plus 1 page cover and publishing information, Marcel Dekker, Inc.

* cited by examiner

METHOD FOR MAKING POLYALPHAOLEFINS USING ALUMINUM HALIDE CATALYZED OLIGOMERIZATION OF OLEFINS

TECHNICAL FIELD

The present disclosure relates to a method of making an oligomer product and/or polyalphaolefins. More specifically, the present disclosure relates to a method of making oligomer product and/or polyalphaolefins using aluminum halide catalyzed oligomerization of olefins (e.g., normal alpha olefins, linear internal olefins, etc.).

BACKGROUND

Oligomer products, hydrogenated oligomer products (e.g., polyalphaolefins) and their derivatives are used for the production of a wide variety of articles (e.g., synthetic lubricants or lubricant additives). The use of a particular oligomer product and/or hydrogenated oligomer product in a particular application will depend on the type of physical and/or mechanical properties displayed by the oligomer product and/or hydrogenated oligomer product, and such properties can be a result of the method used for producing a particular oligomer product and or hydrogenated oligomer product, e.g., the reaction conditions under which the oligomer product is produced. Thus, there is an ongoing need to develop and improve methods for producing these oligomers.

SUMMARY

In an aspect, the present disclosure is directed to a process contacting an aluminum halide and monomer comprising olefins to form an oligomer product. In another aspect, the present disclosure is directed to a process comprising contacting 1) a catalyst mixture comprising i) an aluminum trihalide and ii) an organic liquid carrier comprising first olefins, the organic liquid carrier olefins comprising at least 75 mole % 1,2-disubstituted olefins, trisubstituted olefins, or any combination thereof and 2) a monomer comprising olefins to form an oligomer product. In a further embodiment, the present disclosure is directed to process comprising a) contacting a catalyst comprising an aluminum halide and monomer comprising second olefins to form an oligomer product, b) separating at least a portion of the oligomer product from the monomer, and c) hydrogenating the separated oligomer product to form a polyalphaolefin. In yet another aspect, the present disclosure is directed to a process comprising a) contacting 1) a catalyst mixture comprising i) an aluminum trihalide and ii) an organic liquid carrier comprising first olefins, the organic liquid carrier olefins comprising at least 75 mole % 1,2-disubstituted olefins, trisubstituted olefins, or any combination thereof, 2) a monomer comprising second olefins to form an oligomer product, b) separating at least a portion of the oligomer product from the monomer product, and c) hydrogenating the separated oligomer product to form a polyalphaolefin.

In an embodiment, the aluminum halide can be an aluminum trihalide. In an embodiment, the organic liquid carrier olefins can comprise at least 75 mole % 1,2-disubstituted olefins, trisubstituted olefins, or any combination thereof; alternatively, at least 75 mole % 1,2-disubstituted olefins; or alternatively, at least 75 mole % trisubstituted olefins. In some embodiments, the organic liquid carrier olefins can be $C_6$ to $C_{24}$ disubstituted olefins, $C_6$ to $C_{24}$ trisubstituted olefins, or any combination thereof; alternatively, $C_6$ to $C_{24}$ disubstituted olefins; or alternatively, $C_6$ to $C_{24}$ trisubstituted olefins. In some embodiments, the organic liquid carrier olefins can comprise less than 5 mole % alpha olefins; alternatively, less than 20 mole % tetrasubstituted olefins; or alternatively, less than 5 mole % alpha olefins and less than 20 mole % tetrasubstituted olefins. In an embodiment, the monomer can comprise a $C_3$ to $C_{30}$ olefins. In some embodiments, the monomer can comprise alpha olefins; or alternatively, 1-hexene, 1-octene, 1-decene, 1-dodecene, 1-tetradecene, or any combination thereof.

In an embodiment, the catalyst mixture can further comprise a promoter. In other embodiments, the aluminum halide (or catalyst mixture), the monomer, and a promoter are contacted to form an oligomer product. In some embodiment the promoter can comprise water, an alcohol, a carboxylic acid, an ester, a ketone, an ether, a halogenated hydrocarbon, or any combination thereof. In an embodiment, the catalyst system mixture can comprise a metal halide, an alkyl metal halide, an alkyl metal compound, or any combination thereof; or alternatively, catalyst mixture, the monomer, and a metal halide, an alkyl metal halide, an alkyl metal compound, or any combination thereof are contacted to form an oligomer product.

Disclosed herein is a process comprising contacting 1) a catalyst mixture comprising i) an aluminum trihalide and ii) an organic liquid carrier comprising first olefins, wherein the organic liquid carrier first olefins comprise at least 60 mole % 1,2-disubstituted olefins, trisubstituted olefins, or any combination thereof; and 2) a monomer comprising second olefins to form an oligomer product.

Also disclosed herein is an oligomer product produced by the process comprising contacting 1) a catalyst mixture comprising i) an aluminum trihalide and ii) an organic liquid carrier comprising first olefins, wherein the organic liquid carrier olefins comprise at least 75 mole % 1,2-disubstituted olefins, trisubstituted olefins, or any combination thereof; and 2) a monomer comprising second olefins to form an oligomer product.

Further disclosed herein is a polyalphaolefin produced by the process comprising a) contacting 1) a catalyst mixture comprising i) an aluminum trihalide and ii) an organic liquid carrier comprising first olefins, wherein the organic liquid carrier olefins comprises at least 75 mole % 1,2-disubstituted olefins, trisubstituted olefins, or any combination thereof; and 2) a monomer comprising second olefins to form an oligomer product; b) separating at least a portion of the oligomer product from the monomer, to yield a separated oligomer product; and c) hydrogenating the separated oligomer product to form a polyalphaolefin.

DETAILED DESCRIPTION

Disclosed herein are methods of making an oligomer product and/or polyalphaolefins. In an embodiment, a method of the present disclosure comprises oligomerizing one or more olefin monomers in the presence of a catalyst (e.g., an oligomerization catalyst, such as for example an aluminum halide) to produce an oligomer product. At least a portion of the oligomer product can be recovered and/or hydrogenated to produce what is commonly referred to as polyalphaolefins (PAOs). In an embodiment, such method can result in PAOs with desirable properties, e.g., viscosity.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2$^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News*, 63(5), 27, 1985. In some instances a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms can be utilized to indicate the presence or absence of a particular substituent, a particular regiochemistry and/or stereochemistry, or the presence or absence of a branched underlying structure or backbone.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. The term "consisting essentially of" occupies a middle ground between closed terms like "consisting of" and fully open terms like "comprising." Absent an indication to the contrary, when describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to feature class to which is utilized and it is possible to have different transitional terms or phrases utilized with different features within a claim. For example a method can comprise several recited steps (and other non-recited steps) but utilize a catalyst system preparation consisting of specific or alternatively consisting essentially of specific steps but utilize a catalyst system comprising recited components and other non-recited components.

While compositions and methods are described in terms of "comprising" (or other broad term) various components and/or steps, the compositions and methods can also described using narrower terms such as "consist essentially of" or "consist of" the various components and/or steps.

Use of the term "optionally" with respect to any element of a claim is intended to mean that the subject element is required, or alternatively, is not required. Both alternatives are intended to be within the scope of the claim.

The terms "a," "an," and "the" are intended, unless specifically indicated otherwise, to include plural alternatives, e.g., at least one. For any particular compound or group disclosed herein, any name or structure presented is intended to encompass all conformational isomers, regioisomers, and stereoisomers that can arise from a particular set of substituents, unless otherwise specified. For example, a general reference to pentane includes n-pentane, 2-methylbutane, and 2,2-dimethylpropane and a general reference to a butyl group includes an n-butyl group, a sec-butyl group, an iso-butyl group, and t-butyl group or tert-butyl group. The name or structure also encompasses all enantiomers, diastereomers, and other optical isomers whether in enantiomeric or racemic forms, as well as mixtures of stereoisomers, as would be recognized by a skilled artisan, unless otherwise specified.

The term "olefin" whenever used in this specification and claims refers to compounds that have at least one carbon-carbon double bond that is not part of an aromatic ring or an aromatic ring system. The term "olefin" includes aliphatic and aromatic, cyclic and acyclic, and/or linear and branched compounds having at least one carbon-carbon double bond that is not part of an aromatic ring or ring system unless specifically stated otherwise. The term "olefin," by itself, does not indicate the presence or absence of heteroatoms unless explicitly indicated. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s). The term "hydrocarbon olefin" refers to olefin compounds containing only hydrogen and carbon.

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. For example, alkamonoenes, alkadienes, and alkatrienes refer to a linear or branched acyclic hydrocarbon olefins having only one carbon-carbon double bond (acyclic having a general formula of $C_nH_{2n}$), only two carbon-carbon double bonds (acyclic having a general formula of $C_nH_{2n-2}$, and only three carbon-carbon double bonds (acyclic having a general formula of $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a carbon-carbon double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a carbon-carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "consists essentially of normal alpha olefin(s)," or variations thereof, whenever used in this specification and claims refers to commercially available normal alpha olefin product(s). The commercially available normal alpha olefin product can contain non-normal alpha olefin impurities such as vinylidenes, internal olefins, branched alpha olefins, paraffins, and diolefins, among other impurities, which are not removed during the normal alpha olefin production process. One readily recognizes that the identity and quantity of the specific impurities present in the commercial normal alpha olefin product will depend upon the source of commercial normal alpha olefin product. Consequently, the term "consists essentially of normal alpha olefins" and its variants is not intended to limit the amount/quantity of the non-linear alpha olefin components any more stringently than the amounts/quantities present in a particular commercial normal alpha olefin product unless explicitly stated.

The term "1,2-disubstituted olefin" as used herein refers to a compound having at least one carbon-carbon double bond and having one and only one substituent located on each carbon atom of the carbon-carbon double bond(s). The term "1,2-disubstituted olefin" by itself does not indicate the presence or absence of heteroatoms unless explicitly indicated. The term "hydrocarbon 1,2-disubstituted olefin" refers to a 1,2-disubstituted olefin not having any heteroatoms. It should be noted that hydrocarbon 1,2-disubstituted olefin compositions utilized within the present disclosure can contain minor (less than 300 ppm by weight) impurities which can have heteroatoms. The term "trisubstituted olefin" as used herein refers to a compound having at least one carbon-carbon double bond where there are two substituents attached to one carbon of the olefin carbon-carbon double bond and one and only one substituent attached to the other carbon atom of the olefin carbon-carbon double bond. The term "trisubstituted olefin" by itself does not indicate the presence or absence of heteroatoms unless explicitly indicated. The term "hydrocarbon trisubstituted olefin" refers to a trisubstituted olefin not having any heteroatoms. It should be noted that hydrocarbon trisubstituted olefin compositions utilized within the present disclosure can contain minor (less than 300 ppm by weight) impurities which can have heteroatoms.

As used within this specification, the phrases "in the substantial absence of an organic diluent," "in the absence of an organic diluent," "in the absence of organic solvents," "in the substantial absence of an organic solvent," and similar phrases refer to forming the oligomer product under conditions wherein the monomer concentration is not substantially reduced by non-reactive components (with the exception compounds present in the organic liquid carrier which can be utilized in the catalyst mixture within some aspects and embodiment disclosed herein). As will be apparent to one skilled in the art and with the help of this disclosure, the terms "organic diluent" and "organic solvent" refer to specific compound(s) that are introduced to reduce the concentration of the reactive monomers or to serve specific function in the process, e.g., moderating the heat of reaction or providing fluidity to the reaction solution, and do not function as a reactant within the oligomerization. Thus, the phrases "in the absence of an organic diluent," "in the substantial absence of an organic diluent," "in the absence of organic solvents," "in the substantial absence of an organic solvent," and similar phrases are not intended as limiting the invention to the complete absence of compounds that are impurities within the monomer feedstocks or feedstreams which under other circumstances or in greater quantities could be construed to act as a diluent or solvent. For example, while decane could be an "organic diluent" or "organic solvent" under certain circumstances, the presence of small or minor amounts (e.g., about <1.5 percent) of decane as an impurity in a 1-decene monomer stream does not substantially reduce the concentration of 1-decene or serve a specific function within the reaction system and thus would not be excluded by the use of the phrases "in the absence of an organic diluent," "in the substantial absence of an organic diluent," "in the absence of organic solvents," "in the substantial absence of a solvent," or similar terms. It should be noted that for the purpose of the present application, the organic diluent (or the substantial lack thereof) is a separate and distinct element from the organic liquid carrier which can be utilized for the catalyst mixture.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum values can be alternatively stated as "at least" or "greater than or equal to" any recited minimum value for the feature disclosed herein. Features within this disclosure that are provided as a maximum values can be alternatively stated as "less than or equal to" any recited maximum value for the feature disclosed herein.

Processes and/or methods described herein utilize steps, features, and compounds which are independently described herein. The process and methods described herein may or may not utilize step identifiers (e.g., 1), 2), etc., a), b), etc., or i), ii), etc.), features (e.g., 1), 2), etc., a), b), etc., or i), ii), etc.), and/or compound identifiers (e.g., first, second, etc.). However, it should be noted that processes and/or methods described herein can have multiple steps, features (e.g. reagent ratios, formation conditions, among other considerations), and/or multiple compounds having the same general descriptor. Consequently, it should be noted that the processes and/or methods described herein can be modified to use an appropriate step or feature identifier (e.g., 1), 2), etc., a), b), etc., or i), ii), etc.) and/or compound identifier (e.g., first, second, etc.) regardless of step, feature, and/or compound identifier utilized in the a particular aspect and/or embodiment described herein and that step or feature identifiers can be added and/or modified to indicate individual different steps/features/compounds utilized within the process and/or methods without detracting from the general disclosure.

Embodiments disclosed herein can provide the materials listed as suitable for satisfying a particular feature of the embodiment delimited by the term "or." For example, a particular feature of the disclosed subject matter may be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

In an aspect, the present disclosure provides a process to form an oligomer product. Disclosed herein processes comprising contacting a catalyst and a monomer comprising olefins to form an oligomer product; alternatively, contacting an aluminum halide compound and a monomer comprising olefins to form an oligomer product; or alternatively, contacting an aluminum trihalide and a monomer comprising olefins to form an oligomer product. In an embodiment, processes disclosed herein can comprise contacting 1) a catalyst mixture (or catalyst system mixture); and 2) a monomer comprising olefins to form an oligomer product. In another embodiment, processes disclosed herein can comprise contacting 1) a catalyst mixture (or catalyst system mixture) comprising i) an aluminum trihalide (or an aluminum halide compound) and ii) an organic liquid carrier; and 2) a monomer comprising olefins to form an oligomer product. In a further embodiment, processes disclosed herein can comprise contacting a 1) a catalyst mixture (or catalyst system mixture) comprising i) an aluminum trihalide (or an aluminum halide compound), ii) a promoter, and iii) an organic liquid carrier; and 2) a monomer comprising olefins to form an oligomer product. In yet another embodiment, processes disclosed herein can comprise contacting 1) a catalyst mixture (or catalyst system mixture) comprising i) an aluminum trihalide (or an aluminum halide compound) and ii) an organic liquid carrier; 2) a promoter; and 3) a monomer comprising olefins to form an oligomer product.

In another aspect, the present disclosure provides a process to produce polyalphaolefins from an oligomer product produced by any process described herein. In an embodiment, processes disclosed herein can comprise: a) contacting 1) a catalyst mixture (or a catalyst system mixture) and 2) a monomer comprising olefins to form an oligomer product; b) separating the oligomer product (or a portion of the oligomer product) from the monomer, to yield a separated oligomer product; and c) hydrogenating the separated oligomer product (or portion of the separated oligomer product) to form a polyalphaolefin; alternatively, a) contacting 1) an aluminum halide compound (or mixture comprising an aluminum halide compound); and 2) a monomer comprising olefins to form an oligomer product; b) separating the oligomer product (or at least a portion of the oligomer product) from the monomer, to yield a separated oligomer product; and c) hydrogenating the separated oligomer product (or portion of the separated oligomer product) to form a polyalphaolefin; or alternatively, a) contacting 1) an aluminum trihalide (or mixture comprising an aluminum trihalide); and 2) a monomer comprising olefins to form an oligomer product; b) separating at least a portion of the oligomer product from the monomer, to yield a separated oligomer product; and c) hydrogenating the separated oligomer product (or portion of the separated oligomer product) to form a polyalphaolefin. In an embodiment, processes disclosed herein can comprise: a) contacting 1) a catalyst mixture (or catalyst system mixture) comprising i) an aluminum trihalide (or an aluminum halide compound) and ii) an organic liquid carrier, and 2) a monomer comprising olefins to form an oligomer product; b) separating the oligomer product (or at least a portion of the oligomer product) from the monomer, to yield a separated oligomer product; and c) hydrogenating the separated oligomer product (or portion of the separated oligomer product) to form a polyalphaolefin product. In another embodiment, processes disclosed herein can comprise a) contacting 1) a catalyst mixture (or catalyst system mixture) comprising i) an aluminum trihalide (or an aluminum halide compound) and ii) an organic liquid carrier, and 2) a monomer comprising olefins to form an oligomer product; b) separating the oligomer product (or at least a portion of the oligomer product) from the monomer, to yield a separated oligomer product; and c) hydrogenating the separated oligomer product (or portion of the separated oligomer product) to form a polyalphaolefin. In a further embodiment, processes disclosed herein can comprise a) contacting 1) a catalyst mixture (or catalyst system mixture) comprising i) an aluminum trihalide (or an aluminum halide compound), ii) a promoter, and iii) an organic liquid carrier, and 2) a monomer comprising olefins to form an oligomer product; b) separating the oligomer product (or at least a portion of the oligomer product) from the monomer, to yield a separated oligomer product; and c) hydrogenating the separated oligomer product (or portion of the separated oligomer product) to form a polyalphaolefin. In yet another embodiment, processes disclosed herein can comprise a) contacting 1) a catalyst mixture (or catalyst system mixture) comprising i) an aluminum trihalide (or an aluminum halide compound) and ii) an organic liquid carrier, 2) a promoter; and 3) a monomer comprising olefins to form an oligomer product; b) separating the oligomer product (or at least a portion of the oligomer product) from the monomer, to yield a separated oligomer product; and c) hydrogenating the separated oligomer product (or portion of the separated oligomer product) to form a polyalphaolefin.

In an embodiment of these processes, the oligomer product can be formed under conditions capable of forming an oligomer product. In an aspect, the oligomer product can be formed in the substantial absence of an organic diluent. In another aspect the oligomer product can be formed in the presence of an organic diluent. In an embodiment of the appropriate processes, the processes can further comprise deactivating the catalyst (or catalyst system), to yield a deactivated catalyst (or catalyst system) alternatively, separating the oligomer product (and optionally the monomer) from the catalyst (or catalyst system); alternatively, separating at least a portion of the oligomer product (and optionally the monomer) from the catalyst (or catalyst system); alternatively, deactivating the catalyst (or catalyst system) and separating the oligomer product (and optionally the monomer) from the deactivated catalyst (or catalyst system); or alternatively, deactivating the catalyst (or catalyst system) and separating at least a portion of the oligomer product (and optionally the monomer) from the deactivated catalyst (or catalyst system). In other embodiments of the appropriate processes, the processes can further comprise hydrogenating the separated oligomer product (or portion of the separated oligomer product) with a hydrogenation catalyst under conditions capable of hydrogenating the oligomer product. In an embodiment of the appropriate processes, the separating the oligomer product (or least a portion of the oligomer product) from the monomer can comprise distilling the oligomer product (or at least a portion of the oligomer product) from the monomer. In a further embodiment of the appropriate processes, the separating of the oligomer product (or at least a portion of the oligomer product) can comprise forming a composition (or alternatively, one or more compositions) comprising, or consisting essentially of, a trimer or higher oligomer of the oligomer product. In yet another embodiment of the appropriate processes, the polyalphaolefin can be separated into two or more compositions comprising, or consisting essentially of, polyalphaolefins having different nominal viscosities (e.g., different 100° C. kinematic viscosities).

Generally, the catalyst, catalyst mixture, catalyst system, catalyst system mixture, monomer, aluminum halide compound, aluminum trihalide, promoter, organic liquid carrier, oligomer product, conditions capable of forming an oligomer product, the catalyst deactivation (or catalyst system deactivation), the separations (or the oligomer product(s) or polyalphaolefin composition(s)), the hydrogenation catalyst, the condition capable of hydrogenating the separated oligomer product(s) are independent elements of the appropriate processes described herein. Aspects and embodiments of the catalyst, catalyst mixture, catalyst system, catalyst system mixture, monomer, aluminum halide compound, aluminum trihalide, promoter, organic liquid carrier, oligomer product, conditions capable of forming an oligomer product, the catalyst deactivation (or catalyst system deactivation), the separations (or the oligomer product(s) or polyalphaolefin composition(s)), the hydrogenation catalyst, the condition capable of hydrogenating the separated oligomer product(s) are independently described herein and their independently described aspects and/or embodiments descriptions can be combined in fashion to provide further processes envisioned and contemplated by the present disclosure.

In an embodiment, the monomer can comprise, or consist essentially of, one or more alpha olefins, one or more normal alpha olefins, one or more internal olefins, one or more branched olefins, or combinations thereof. In some embodiments, the monomer (alpha olefin, internal olefin, and/or branched olefin) can be a hydrocarbon olefin. In other embodiments, the monomer (alpha olefin, internal olefin, and/or branched olefin) can be an aliphatic olefin. In further embodiments, the monomer (alpha olefin, internal olefin, and/or branched olefin) can be an aliphatic hydrocarbon olefin. In an embodiment, the monomer can comprise, or consist essentially of, one or more normal alpha olefins. In another embodiment, the alpha olefin (or the normal alpha olefin) which can be utilized as the monomer can comprise, consist essentially of, or can be, one or more normal alpha olefins. In an embodiment, the monomer can comprise, or consist essentially of, second olefins (as opposed to first olefins). In an embodiment, the second olefins of the monomer can be any of the olefins disclosed herein as being the monomer (or as part of the monomer), such as for example one or more alpha olefins, one or more normal alpha olefins, one or more internal olefins, one or more branched olefins, or combinations thereof.

A wide range of monomer carbon numbers can be utilized in the process. For example, the processes described herein can be applicable to monomers as small as propylene and as large as waxes having 70 or 75 carbon atoms. In any aspect and/or in any embodiment described herein, the monomer can comprise, or consist essentially of, or can be, a $C_3$ to $C_{70}$ olefin; alternatively, a $C_3$ to $C_{40}$ olefin; alternatively, a $C_3$ to $C_{30}$ olefin; alternatively, a $C_4$ to $C_{20}$ olefin; alternatively, a $C_5$ to $C_{18}$ olefin; alternatively, a $C_6$ to $C_{16}$ olefin; alternatively, a $C_6$ to $C_{14}$ olefin; or alternatively, a $C_8$ to $C_{12}$ olefin. In any aspect and/or in any embodiment described herein, the monomer can comprise, or consist essentially of, or can be, a $C_3$ to $C_{70}$ alpha olefin; alternatively, a $C_3$ to $C_{40}$ alpha olefin; alternatively, a $C_4$ to $C_{20}$ alpha olefin; alternatively, a $C_5$ to $C_{18}$ alpha olefin; alternatively, a $C_6$ to $C_{16}$ alpha olefin; alternatively, a $C_6$ to $C_{14}$ alpha olefin; or alternatively, a $C_8$ to $C_{12}$ alpha olefin. In an embodiment, the monomer can comprise, or consist essentially of, or can be, a $C_6$ alpha olefin, a $C_8$ alpha olefin, a $C_{10}$ alpha olefin, a $C_{12}$ alpha olefin, a $C_{14}$ alpha olefin, a $C_{16}$ alpha olefin, or any combination thereof; alternatively, a $C_6$ alpha olefin, a $C_8$ alpha olefin, a $C_{10}$ alpha olefin, a $C_{12}$ alpha olefin, a $C_{14}$ alpha olefin, or any combination thereof; alternatively, a $C_8$ alpha olefin, a $C_{10}$ alpha olefin, a $C_{12}$ alpha olefin, or any combination thereof; alternatively, a $C_6$ alpha olefin; alternatively, a $C_8$ alpha olefin; alternatively, a $C_{10}$ alpha olefin; alternatively, a $C_{12}$ alpha olefin; alternatively, a $C_{14}$ alpha olefin; alternatively, a $C_{16}$ alpha olefin; or alternatively, a $C_{18}$ alpha olefin. In any aspect and/or any embodiment described herein, the monomer can comprise, or consist essentially of, or can be, a $C_3$ to $C_{70}$ normal alpha olefin; alternatively, a $C_3$ to $C_{40}$ normal alpha olefin; alternatively, a $C_4$ to $C_{20}$ normal alpha olefin; alternatively, a $C_5$ to $C_{18}$ normal alpha olefin; alternatively, a $C_6$ to $C_{16}$ normal alpha olefin; alternatively, a $C_6$ to $C_{14}$ normal alpha olefin; or alternatively, a $C_8$ to $C_{12}$ normal alpha olefin. In an embodiment, the monomer can comprise, or consist essentially of, or can be, a $C_6$ normal alpha olefin, a $C_8$ normal alpha olefin, a $C_{10}$ normal alpha olefin, a $C_{12}$ normal alpha olefin, a $C_{14}$ normal alpha olefin, a $C_{16}$ normal alpha olefin, or any combination thereof; alternatively, a $C_6$ normal alpha olefin, a $C_8$ normal alpha olefin, a $C_{10}$ normal alpha olefin, a $C_{12}$ normal alpha olefin, a $C_{14}$ normal alpha olefin, or any combination thereof; alternatively, a $C_8$ normal alpha olefin, a $C_{10}$ normal alpha olefin, a $C_{12}$ normal alpha olefin, or any combination thereof; alternatively, a $C_6$ normal alpha olefin; alternatively, a $C_8$ normal alpha olefin; alternatively, a $C_{10}$ normal alpha olefin; alternatively, a $C_{12}$ normal alpha olefin; alternatively, a $C_{14}$ normal alpha olefin; alternatively, a $C_{16}$ normal alpha olefin; or alternatively, a $C_{18}$ normal alpha olefin. In any aspect and/or any embodiment described herein, the monomer can comprise, or consist essentially of, 1-hexene, 1-octene, 1-decene, 1-dodecene, 1-tetradecene, 1-hexadecene, or any combination thereof; alternatively, 1-hexene, 1-octene, 1-decene, 1-dodecene, 1-tetradecene, or any combination thereof; alternatively, 1-octene, 1-decene, 1-dodecene, or any combination thereof. In other embodiments, the monomer can comprise, or consist essentially of, 1-pentene; alternatively, 1-hexene; alternatively, 1-heptene; alternatively, 1-octene; alternatively, 1-nonene; alternatively, 1-decene; alternatively, 1-undecene; alternatively, 1-dodecene; alternatively, 1-tridecene; alternatively, 1-tetradecene; alternatively, 1-pentadecene; alternatively, 1-hexadecene; alternatively, 1-heptadecene; or alternatively, 1-octadecene.

In an embodiment, the monomer can comprise, at least 50 wt. % of any alpha olefin described herein (e.g., a normal alpha olefin, among others described herein). Alternatively, the monomer can comprises at least 55 wt. %, 60 wt. %, 65 wt. %, 70 wt. %, 75 wt. %, 80 wt. %, 82.5 wt. %, 85 wt. %, 87.5 wt. %, 90 wt. %, 91 wt. %, 92 wt. %, 93 wt. %, 94 wt. %, 95 wt. %, 96 wt. %, 97 wt. %, or 98 wt. % of any alpha olefin described herein (e.g., a normal alpha olefin, among others described herein). The wt. % of the components of the monomer are based upon the total weight of the monomer.

In an embodiment, the monomer can be a normal alpha olefin. Generally, the normal alpha olefin can be produced by any process which can produce a normal alpha olefin having the purity acceptable for the herein described processes. One readily available source of a normal alpha olefin monomer applicable to the herein described process includes without limitation the products from the oligomerization of ethylene. Commercially available normal alpha olefins produced by ethylene oligomerization are available from Chevron Phillips Chemical Company, LP, Shell, Ineos, Mitsubishi, and Idemitsu among other sources. Depending upon the particular process and alpha carbon number, the normal alpha olefin content of the commercial normal alpha olefin feedstocks can vary. However, all are generally usable within the process disclosed herein.

Generally, the catalyst (or catalyst system) can be any compound (or combination of compounds) which can oligomerize the monomer. In an embodiment, the catalyst can, comprise, consist essentially of, or consist of, an aluminum halide compound. In an embodiment, the aluminum halide compound can have the formula $R_yAlX_{3-y}$ wherein R is a hydrocarbyl group (or an alkyl group), X is a halide, and y can range from 0 to less than 3. In some embodiments y can range from greater than 0 to less than 3; alternatively, y can range from 0 to 2; alternatively, y can be 0; alternatively, y can be about 1; alternatively, y can be about 1.5; or alternatively, y can be about 2. In some embodiments, each halide of the aluminum trihalide or aluminum halide compound having the formula $R_yAlX_{3-y}$ independently can be chloride, bromide, or iodide; alternatively, chloride or bromide; alternatively, chloride or iodide; or alternatively, bromide or iodide. When the aluminum halide compound has the formula $R_yAlX_{3-y}$ and y is greater than 1, each R independently can be a $C_1$ to $C_{10}$ hydrocarbyl group; or alternatively, a $C_2$ to $C_6$ hydrocarbyl group. In an embodiment when the aluminum halide compound has the formula $R_yAlX_{3-y}$, the aluminum halide compound can be a hydrocarbylaluminum dihalide, a hydrocarbylaluminum sesquihalide, a dihydrocarbylaluminum halide, or any combination thereof; alternatively, a hydrocarbylaluminum dihalide; alternatively, a hydrocarbylaluminum sesquihalide; or alternatively, a dihydrocarbylaluminum halide. In an embodiment, where the aluminum halide compound has the formula $R_yAlX_{3-y}$ and y is greater than 0, each R independently can be a methyl group, an ethyl group, a propyl group, a butyl group, a pentyl group, a hexyl group, a heptyl group, or a phenyl group; alternatively, an ethyl group, an n-butyl group, an iso-butyl group or a hexyl group; alternatively, an ethyl group; alternatively, an n-butyl group; or alternatively, an iso-butyl group. In some embodiments, the aluminum halide compound can be ethylaluminum dichloride, ethylaluminum dibromide, ethylaluminum sesquichloride, ethylaluminum sesquibromide, diethylaluminum chloride, diethylaluminum bromide, or any combination thereof; alternatively, ethylaluminum dichloride, ethylaluminum sesquichloride, diethylaluminum chloride, or any combination thereof; or alternatively, ethylaluminum dibromide, ethylaluminum sesquibromide, diethylaluminum bromide, or any combination thereof. In some embodiments, the catalyst can, comprise, consist essentially of, or consist of, an aluminum trihalide. In some embodiments, the trihalide can have the formula $AlX_3$ where each X independently can be chloride, bromide, or iodide. Aluminum trihalides suitable for use in the present disclosure can comprise, consist essentially of, or consist of, aluminum trichloride, aluminum tribromide, aluminum triiodide, or any combinations thereof; alternatively, aluminum trichloride, aluminum tribromide, or any combinations thereof; alternatively, aluminum trichloride; or alternatively, aluminum tribromide. In an embodiment, the aluminum halide catalyst is substantially devoid of an aluminum halide based ionic liquid. Within this context, substantially devoid of an aluminum halide based ionic liquid means that less than 5 percent of the aluminum halide is in the form a low melting organic halogen aluminate salt.

Generally, the aluminum halide to monomer molar ratio can be any ratio which can provide a desirable oligomer product. In an embodiment, the minimum aluminum halide to monomer molar ratio can be $5 \times 10^{-8}$:1, $5 \times 10^{-5}$:1, $1 \times 10^{-4}$:1, $2.5 \times 10^{-4}$:1, $5 \times 10^{-4}$:1, $7.5 \times 10^{-4}$:1 or $1 \times 10^{-3}$:1. In an embodiment, the maximum aluminum halide to monomer molar ratio can be $3.5 \times 10^{-2}$:1, $3 \times 10^{-2}$:1, $2.5 \times 10^{-2}$:1, $2 \times 10^{-2}$:1, $1.5 \times 10^{-2}$:1, $1 \times 10^{-2}$:1, or $1.1 \times 10^{-2}$:1. In an embodiment, the aluminum halide to monomer molar ratio can range from any minimum aluminum halide to monomer molar ratio described herein to any maximum aluminum halide to monomer molar ratio described herein. Suitable ranges for the aluminum halide to monomer molar ratio can include, but are not limited to, from $5 \times 10^{-8}$:1 to $1.1 \times 10^{-2}$:1, from $5 \times 10^{-5}$:1 to $3.5 \times 10^{-2}$:1, from $1 \times 10^{-4}$:1 to $3 \times 10^{-2}$:1, from $2.5 \times 10^{-4}$:1 to $2.5 \times 10^{-2}$:1, from $5 \times 10^{-4}$:1 to $2 \times 10^{-2}$:1, from $5 \times 10^{-4}$:1 to $1.5 \times 10^{-2}$:1, from $5 \times 10^{-4}$:1 to $1 \times 10^{-2}$:1, or from $5 \times 10^{-4}$:1 to $5 \times 10^{-3}$:1. Other suitable aluminum halide to monomer molar ratio ranges are readily apparent from the present disclosure.

In an embodiment, stable liquid solutions can be formed between aluminum halides and an organic liquid carrier comprising first olefins (as opposed to second olefins) where the organic liquid carrier first olefins comprise, consist essentially of, or consist of, one or more 1,2-disubstituted olefins, trisubstituted olefins, or any combination thereof. This solution can be prepared in advance of its use and stored for long periods of time. The formation of catalyst mixtures comprising, consisting essentially of, or consisting of, an aluminum halide and an organic liquid carrier comprising olefins (e.g., first olefins) where the organic liquid carrier olefins (e.g., organic liquid carrier first olefins) comprise, consist essentially of, or consists of, one or more 1,2-disubstituted olefins, trisubstituted olefins, or any combination thereof has an advantage in that the catalyst mixture can thus avoid the addition of solid/powered catalyst (e.g., an aluminum trihalide) to a reaction, does not add unreactive components to a reaction (e.g., oligomerization), and/or the catalyst mixture can be stable for long periods of time. In some embodiments, the catalyst mixture comprising, consisting essentially of, or consisting of an aluminum halide (e.g., an aluminum trihalide) and an organic liquid carrier comprising olefins (e.g., first olefins) where the organic liquid carrier olefins (e.g., organic liquid carrier first olefins) comprises, consists essentially of, or consists of, one or more 1,2-disubstituted olefins, trisubstituted olefins, or any combination thereof can be stored for at least 1 day, 7 days, 14 days, 30 days or 60 days.

In aspects and embodiments utilizing a catalyst mixture including an organic liquid carrier, the organic liquid carrier can comprise, or consist essentially of, olefins (e.g., first olefins). In an embodiment, the organic liquid carrier can comprise at least 50 wt. %, 55 wt. %, wt. %, 65 wt. %, 70 wt. %, 75 wt. %, 80 wt. %, 85 wt. %, 90 wt. %, 92 wt. %, 94 wt. %, or 95 wt. % olefins (e.g., first olefins). In an embodiment, the catalyst mixture including an organic liquid carrier, the organic liquid carrier olefins (e.g., organic liquid carrier first olefins) can comprise 1,2-disubstituted olefins, trisubstituted olefins, or any combination thereof; alternatively, 1,2-disubstituted olefins; or alternatively, trisubstituted olefins. In some embodiments, the organic liquid carrier olefins (1,2-disubstituted olefins, trisubstituted olefins, or combination thereof) can be hydrocarbon olefins. In other embodiments, the organic liquid carrier olefins (1,2-disubstituted olefins, trisubstituted olefins, or combination thereof) can be aliphatic olefins. In further embodiments, the organic liquid carrier olefins (1,2-disubstituted olefins, trisubstituted olefins, or combination thereof) can be aliphatic hydrocarbon olefins. In some embodiments, the 1,2-disubstituted olefins which can be utilized as the organic liquid carrier olefins (e.g., organic liquid carrier first olefins) or as part of the organic liquid carrier olefins (e.g., organic liquid carrier first olefins) can comprise, consist essentially of, or consist of linear 1,2-disubstituted olefins, branched (at a position other than on the olefin carbon-carbon double bond) olefins, or any combination thereof; alternatively, linear 1,2-disubstituted olefins; or alternatively, branched 1,2-disubstituted olefins. In an embodiment, the liquid organic carrier olefins can comprise at least 50 mole %, 55 mole %, 60 mole %, 65 mole %, 70 mole %, 75 mole %, 80 mole %, 85 mole %, 90 mole %, 92 mole %, 94 mole %, or 95 mole % of any 1,2-disubstituted olefin, trisubstituted olefin, or combination thereof described herein. In some embodiments, the liquid organic carrier olefins can comprise a maximum of 10 mole %, 8 mole %, 6 mole %, 5 mole %, 4 mole %, 3 mole %, or 2 mole % of any alpha olefin (or normal alpha olefin); for example any alpha olefin (or normal alpha olefin) described herein. In some embodiments, the liquid organic carrier olefins can comprise a maximum of 50 mole %, 45 mole %, 40 mole %, 35 mole %, 30 mole %, 25 mole %, 20 mole %, 15 mole %, 10 mole %, 8 mole %, 6 mole %, or 5 mole % tetrasubstituted olefins. In some embodiments, the liquid organic carrier olefins can comprise a maximum of 30 mole %, 25 mole %, 20 mole %, 15 mole %, 10 mole %, 8 mole %, 6 mole %, or 5 mole % vinylidenes. In some embodiments, the liquid organic carrier can comprise a maximum of 100 ppm (by weight), 80 ppm, 60 ppm, 50 ppm, 40 ppm, 30 ppm, 20 ppm or 10 ppm water (unless intentionally added as the promoter described herein). In some embodiments, the liquid organic carrier can comprise a maximum of 1000 ppm (by weight), 750 ppm, 500 ppm, 250 ppm, 100 ppm, 80 ppm, 60 ppm, 50 ppm, 40 ppm, 30 ppm, 20 ppm or 10 ppm peroxides (unless intentionally added as the promoter described herein).

A wide range of 1,2-disubstituted olefin and/or trisubstituted olefin carbon numbers can be utilized as the olefins (e.g., first olefins) in the organic liquid carrier for the appropriate processes described herein. For example, the 1,2-disubstituted olefins and/or trisubstituted olefins which can be utilized as the olefins (e.g., first olefins) in the organic liquid carries can individually comprise, consist essentially of, or consist of, $C_6$ to $C_{24}$ olefins (e.g., $C_6$ to $C_{24}$ disubstituted olefins and/or $C_6$ to $C_{24}$ trisubstituted olefins); alternatively, $C_6$ to $C_{20}$ olefins (e.g., $C_6$ to $C_{20}$ disubstituted olefins and/or $C_6$ to $C_{20}$ trisubstituted olefins); alternatively, $C_6$ to $C_{16}$ olefins (e.g., $C_6$ to $C_{16}$ disubstituted olefins and/or $C_6$ to $C_{16}$ trisubstituted olefins); alternatively, $C_6$ to $C_{14}$ olefins (e.g., $C_6$ to $C_{14}$ disubstituted olefins and/or $C_6$ to $C_{14}$ trisubstituted olefins); or alternatively, $C_8$ to $C_{12}$ olefins (e.g., $C_8$ to $C_{12}$ disubstituted olefins and/or $C_8$ to $C_{12}$ trisubstituted olefins).

In an embodiment, the 1,2-disubstituted olefins and/or trisubstituted olefins which can be utilized as the olefins (e.g., first olefins) in the organic liquid carrier for the appropriate processes described herein can comprise, or consist essentially of, or can be, $C_6$ olefins, $C_8$ olefins, $C_{10}$ olefins, $C_{12}$ olefins, $C_{14}$ olefins, $C_{16}$ olefins, or any combination thereof; alternatively, $C_6$ olefins, $C_8$ olefins, $C_{10}$ olefins, $C_{12}$ olefins, $C_{14}$ olefins, or any combination thereof; alternatively, $C_8$ olefins, $C_{10}$ olefins, $C_{12}$ olefins, or any combination thereof; alternatively, $C_6$ olefins; alternatively, $C_8$ olefins; alternatively, $C_{10}$ olefins; alternatively, $C_{12}$ olefins; alternatively, $C_{14}$ olefins; alternatively, $C_{16}$ olefins; or alternatively, $C_{18}$ olefins. In an embodiment, the olefins (e.g., first olefins) in the organic liquid carrier can comprise a minimum of 60 wt. %, 70 wt. %, 75 wt. %, 80 wt. %, 85 wt. %, 90 wt. % 92 wt. %, 94 wt. %, 95 wt. %, 96 wt. %, 97 wt. %, or 98 wt. % of any carbon numbered 1,2-disubstituted olefin(s) and/or trisubstituted olefin described herein. In some embodiments, the 1,2-disubstituted olefin and/or trisubstituted olefin utilized as the olefins (e.g., first olefins) in the organic liquid carrier can have the same carbon number as a monomer utilized in the processes described herein; or alternatively, a 1,2-disubstituted olefins and/or trisubstituted olefin utilized as the olefins (e.g., first olefins) in the organic liquid carrier can have a different carbon number as a monomer utilized in the processes described herein.

In an embodiment, the 1,2-disubstituted olefins which can be utilized as the olefins (e.g., first olefins) in the organic liquid carrier, or as a portion of the olefins (e.g., first olefins) in the organic liquid carrier, can be those produced by the isomerization of an alpha olefin (hydrocarbon alpha olefin, linear alpha olefin, linear hydrocarbon alpha olefin, and/or normal alpha olefin). Processes for isomerizing alpha olefins are well known to those having ordinary skill in the art. In an embodiment, trisubstituted olefins which can be utilized as the olefins (e.g., first olefins) in the organic liquid carrier, or as a portion of the olefins (e.g., first olefins) of the organic liquid carrier, can be those produced by the isomerization of vinylidene (e.g., a hydrocarbon vinylidene). Methods for producing vinylidenes are well known by those having ordinary skill in the art; e.g., vinylidenes can be produced by dimerizing alpha olefin with alkylaluminum compounds, zirconium catalysts, and/or metallocene catalysts, among others (e.g., U.S. Pat. Nos. 4,658,078; 4,973,788; and 5,087,788, among others). In an embodiment, the composition comprising the vinylidene can be a composition comprising a dimer fraction from olefin oligomerization process utilizing a metallocene catalyst; e.g., U.S. Publication Nos 2010/0317904; and 2008/0146469; U.S. Pat. Nos. 6,548,723; 7,989,670; and 8,207,390, among others, disclose processes which produce dimer fraction containing vinylidene olefins). Processes for isomerizing vinylidene are well known to those having ordinary skill in the art (e.g., U.S. Pat. Nos. 3,940,452; 4,697,040; 6,407,302; 6,639,118; and 7,078.579, among others).

If present, the alpha olefins which can be present in the organic liquid carrier olefins (e.g., organic liquid carrier first olefins) can be hydrocarbon alpha olefins, linear alpha olefins, linear hydrocarbon alpha olefins, and/or normal alpha olefins; alternatively, linear hydrocarbon alpha olefins; or alternatively, normal alpha olefins. In an embodiment, the 1,2-disubstituted olefins which can be utilized as olefins (e.g., first olefins) in the organic liquid carrier, or a portion of the olefins (e.g., first olefins) of the organic liquid carrier, can be any alpha olefin (or normal alpha olefin) which can be utilized as the monomer (e.g., second olefins) that has been isomerized (i.e., isomerized alpha olefin or isomerized normal alpha olefin) and has the requisite properties of the organic liquid carrier olefins (e.g., organic liquid carrier first olefins). If present, the vinylidenes which can be present in the organic liquid carrier olefins (e.g., organic liquid carrier first olefins) can be hydrocarbon vinylidenes. In an embodiment, the trisubstituted olefins which can be utilized as olefins (e.g., first olefins) in the organic liquid carrier, or a portion of the olefins (e.g., first olefins) in the organic liquid carrier, can be any isomerized vinylidene (or isomerized hydrocarbon vinylidene) which has the requisite properties of the organic liquid carrier olefins (e.g., organic liquid carrier first olefins). In some embodiments, the vinylidenes which can be present in the organic liquid carrier olefins (e.g., organic liquid carrier first olefins) can be those present in the alpha olefin which has been isomerized to form 1,2-disubstituted olefin to be utilized as olefins (e.g., first olefins) in the organic liquid carrier or as a portion of the olefins (e.g., first olefins) in the organic liquid carrier. In other embodiments, the vinylidenes which can be present in the organic liquid carrier olefins (e.g., organic liquid carrier first olefins) can be those remaining after a composition comprising vinylidenes has been isomerized to form trisubstituted olefins to be utilized as olefins (e.g., first olefins) in the organic liquid carrier or as a portion of olefins (e.g., first olefins) in the organic liquid carrier.

Generally, the concentration of the catalyst (e.g., any aluminum halide described herein) in relation to the organic liquid carrier olefins (e.g., organic liquid carrier first olefins) can be any concentration which forms a stable solution with the organic liquid carrier. In an embodiment, the minimum concentration of the catalyst (e.g., any aluminum halide described herein) in the organic liquid carrier olefins (e.g., organic liquid carrier first olefins) can be 0.15 molal (moles catalyst per kg organic liquid carrier), 0.2 molal, 0.4 molal, 0.6 molal, 0.7 molal, 0.8 molal, 0.9 molal, 1.0 molal, 1.1 molal, or 1.2 molal. In an embodiment, the maximum concentration of the catalyst (e.g., any aluminum halide described herein) in the organic liquid carrier olefins can be 4.0 molal, 3.5 molal, 3.0 molal, 2.5 molal, 2.0 molal, 1.8 molal, 1.6 molal, 1.4 molal, 1.2 molal, or 1.0 molal. In an embodiment, the catalyst concentration in the organic liquid carrier olefins (e.g., organic liquid carrier first olefins) can range from any minimum catalyst concentration in the organic liquid carrier olefins described herein to any maximum catalyst concentration in the organic liquid carrier olefins described herein. Suitable ranges for the catalyst concentration in the organic liquid carrier olefins (e.g., organic liquid carrier first olefins) can include, but are not limited to, from 0.15 molal to 4.0 molal, from 0.4 molal to 4.0 molal, from 0.4 molal to 3.5 molal, from 0.6 molal to 3.5 mol, from 0.6 molal to 3.0 molal, or from 0.8 molal to 2.5 molal. Other suitable catalyst concentrations in the organic liquid carrier olefins (e.g., organic liquid carrier first olefins) are readily apparent from the present disclosure.

In an aspect, catalyst systems which can be utilized in the processes described herein can include a promoter. Generally, the promoter can be any compound which can provide a more desirable rate of formation of the oligomer product (or rate of monomer oligomerization) when compared to the rate in the absence of the promoter and/or can provide a more desirable oligomer distribution when compared to the oligomer distribution in the absence of the promoter. In an embodiment, the promoter can comprise, consist essentially of, or consist of, water, an alcohol, a carboxylic acid, an ester, a ketone, an ether, a halogenated hydrocarbon, or any combination thereof; alternatively, water, an alcohol, a carboxylic acid, an ester, a ketone, an ether, or any combination thereof; alternatively, water, an alcohol, an ester, or any combination thereof; alternatively, water and an alcohol; alternatively, water and a carboxylic acid; alternatively, water and an ester, alternatively, water and a ketone; alternatively, an alcohol and a carboxylic acid; alternatively, and alcohol and an ester; alternatively, and alcohol and a ketone; alternatively, water; alternatively, an alcohol; alternatively, a carboxylic acid; alternatively, an ester; alternatively, a ketone; alternatively, an ester, or alternatively, a halogenated hydrocarbon.

In another aspect, the catalyst systems which can be utilized in the process described herein can include a protic promoter. Generally, the protic promoter can be any compound having an acidic proton and can provide a more desirable rate of formation of the oligomer product (or rate of monomer oligomerization) when compared to the rate in the absence of the promoter and/or can provide a more desirable oligomer distribution when compared to the oligomer distribution in the absence of the promoter. In an embodiment, the protic promoter can comprise, consist essentially of, or consist of, water, an alcohol, a carboxylic acid, or any combination thereof; alternatively, water and an alcohol; alternatively, water and a carboxylic acid; alternatively, an alcohol and a carboxylic acid; alternatively, water; alternatively, an alcohol; or alternatively, a carboxylic acid.

Generally, in any aspect or embodiment where water is utilized as the promoter, the water to aluminum halide molar ratio can be any ratio which can provide a more desirable rate of formation of the oligomer product (or rate of monomer oligomerization) when compared to the rate in the absence of the promoter and/or can provide a more desirable oligomer distribution when compared to the oligomer distribution in the absence of the promoter. In an embodiment, the minimum water to aluminum halide molar ratio can be $1 \times 10^{-6}$:1, $5 \times 10^{-6}$:1, $1 \times 10^{-5}$:1, $5 \times 10^{-5}$:1, $1 \times 10^{-4}$:1, $5 \times 10^{-4}$:1, or $1 \times 10^{-3}$:1. In an embodiment, the maximum water to aluminum molar ratio can be 1:1, $5 \times 10^{-1}$:1, $1 \times 10^{-1}$:1, $5 \times 10^{-2}$:1, $1 \times 10^{-2}$:1, $5 \times 10^{-3}$:1, $1 \times 10^{-3}$:1, $5 \times 10^{-4}$:1, or $1 \times 10^{-4}$:1. In an embodiment, the water to aluminum halide molar ratio can range from any minimum water to aluminum halide molar ratio described herein to any maximum water to aluminum halide molar ratio described herein. Suitable ranges for the water to aluminum halide molar ratio can include, but are not limited to, from $1 \times 10^{-6}$:1 to 1:1, from $1 \times 10^{-6}$:1 to $1 \times 10^{-1}$:1, from $1 \times 10^{-6}$:1 to $1 \times 10^{-3}$:1, from $1 \times 10^{-5}$:1 to $1 \times 10^{-1}$:1, from $1 \times 10^{-5}$:1 to $1 \times 10^{-2}$:1, or from $1 \times 10^{-5}$:1 to $1 \times 10^{-3}$:1. Other suitable water to aluminum halide molar ratio ranges are readily apparent from the present disclosure.

In an embodiment, the alcohol that can be utilized as the promoter in any embodiment or aspect of the processes described herein can comprise, consist essentially of, or consist of, a $C_1$ to $C_{20}$, alcohol, a $C_1$ to $C_{15}$, alcohol; alternatively, a $C_1$ to $C_{10}$ alcohol; or alternatively, a $C_1$ to $C_6$ alcohol. In some embodiments, the alcohol can comprise, consist essentially of, or consist of, a monool, a polyol, or any combination thereof; a monool, a diol, or any combination thereof; alternatively, a monool; alternatively, a polyol; or alternatively, a diol. In some embodiments, the alcohol can comprise, consist essentially of, or consist of, a linear alcohol, a branched alcohol, or any combination thereof; alternatively, a linear alcohol; or alternatively a branched alcohol. In some embodiments, alcohol can be an acyclic alcohol, a cyclic alcohol, or any combination thereof; alternatively, an acyclic alcohol; or alternatively, a cyclic alcohol. In other embodiments and independent of whether the alcohol promoter is saturated or olefinic, or acyclic or cyclic, the alcohol which can that can be utilized as the promoter can comprise, consist essentially of, or consist of, a primary alcohol, a secondary alcohol, a tertiary alcohol, or any combination thereof; alternatively, a primary alcohol; alternatively, a secondary alcohol; or alternatively, a tertiary alcohol. In some embodiments, the alcohol can comprise, consist essentially of, or consist of, an aliphatic alcohol, an aromatic alcohol, or any combination thereof; alternatively, an aliphatic alcohol; or alternatively, an aromatic alcohol. In some embodiments, the alcohol can comprise, consist essentially of, or consist of, methanol, ethanol, a propanol, a butanol, a pentanol, a hexanol, or any combination thereof; alternatively, methanol, ethanol, 1-propanol, 2-propanol, 1-butanol, 2-butanol, 2-methyl-propan-1-ol, 1,1-dimethyl-ethan-1-ol (tert-butanol), 1-pentanol, 2 pentanol, 3-pentanol, 3-methylbutan-1-ol, 2,2-dimethylpropan-1-ol, 1-hexanol, 2-hexanol, 3-hexanol, 2-ethylbutan-1-ol, or any combination thereof; alternatively, methanol, ethanol, a propanol, a butanol, a pentanol, a hexanol, or any combination thereof; alternatively, methanol, ethanol, 1-propanol, 1-butanol, 1-pentanol, 1-hexanol, or any combination thereof; alternatively, methanol; alternatively, ethanol; alternatively, 1-propanol; alternatively, 2-propanol; alternatively, 1-butanol; alternatively, 1-pentanol; alternatively, 1-hexanol; or alternatively, 2-ethylbutan-1-ol. In other embodiments, the alcohol can comprise, consist essentially of, or consist of, ethylene glycol, 1,2-propanediol, 1,3-propanediol, 1,2-butanediol, 2,3-butanediol, 1,4-butanediol, 1,5-pentanediol, neopentyl glycol, 1,2-hexanediol, 1,6-hexanediol, 1,2-octanediol, 1,8-octanediol, 1,2-decanediol, 1,10-decanediol, glycerol, 2,2-dimethylolpropane, trimethylolethane, trimethylolpropane, pentaerythritol, dipentaerythritol, sorbitol, 1,2,4-butanetriol, or combinations thereof; alternatively, ethylene glycol; alternatively, 1,2-propanediol; alternatively, 1,3-propanediol; alternatively, 1,2-butanediol; alternatively, 2,3-butanediol; alternatively, 1,4-butanediol; alternatively glycerol; alternatively, trimethylolpropane; or alternatively, pentaerythritol.

Generally, in any aspect or embodiment where an alcohol is utilized as the promoter, the hydroxy group to aluminum halide molar ratio can be any ratio which can provide a more desirable rate of formation of the oligomer product (or rate of monomer oligomerization) when compared to the rate in the absence of the alcohol promoter and/or can provide a more desirable oligomer distribution when compared to the oligomer distribution in the absence of the alcohol promoter. In an embodiment, the minimum hydroxy group to aluminum halide molar ratio can be $1 \times 10^{-3}$:1, $5 \times 10^{-3}$:1, $1 \times 10^{-2}$:1, $5 \times 10^{-2}$:1, or $1 \times 10^{-1}$:1. In an embodiment, the maximum hydroxy group to aluminum molar ratio can be 1.5:1, 1.2:1, 1.1:1, 1:1, $9 \times 10^{-1}$:1, $8 \times 10^{-1}$:1, $7 \times 10^{-1}$:1, $6 \times 10^{-1}$:1, or $5 \times 10^{-1}$:1. In an embodiment, the hydroxy group to aluminum halide molar ratio can range from any minimum hydroxy group to aluminum halide molar ratio described herein to any maximum hydroxy group to aluminum halide molar ratio described herein. Suitable ranges for the hydroxy group to aluminum halide molar ratio can include, but are not limited to, from $1 \times 10^{-3}$:1 to 1.5:1, from $1 \times 10^{-2}$:1 to 1:1, from $1 \times 10^{-2}$:1 to $5 \times 10^{-1}$:1, from $5 \times 10^{-2}$:1 to 1:1, from $5 \times 10^{-2}$:1 to $9 \times 10^{-1}$:1, or from $5 \times 10^{-2}$:1 to $5 \times 10^{-1}$:1. Other suitable hydroxy group to aluminum halide molar ratio ranges are readily apparent from the present disclosure.

In an embodiment, the carboxylic acid that can be utilized as the promoter in any embodiment or aspect of the processes described herein can comprise, consist essentially of, or consist of, a $C_2$ to $C_{20}$ carboxylic acid; a $C_2$ to $C_{15}$ carboxylic acid; alternatively, a $C_3$ to $C_{10}$ carboxylic acid; or alternatively, a $C_3$ to $C_8$ carboxylic acid. In some embodiments, the carboxylic acid can comprise, consist essentially of, or consist of, a mono-carboxylic acid, a poly-carboxylic acid, or any combination thereof; alternatively, a mono-carboxylic acid, a di-carboxylic acid, or any combination thereof; alternatively, a mono-carboxylic acid; alternatively, a poly-carboxylic acid; or alternatively, a di-carboxylic acid. In some embodiments, the carboxylic acid can comprise, consist essentially of, or consist of, a linear carboxylic acid, a branched carboxylic acid, or any combination thereof; alternatively, a linear carboxylic acid; or alternatively a branched carboxylic acid. In some embodiments, the carboxylic acid can be an acyclic carboxylic acid, a cyclic carboxylic acid, or any combination thereof; alternatively, an acyclic carboxylic acid; or alternatively, a cyclic carboxylic acid. In other embodiments, the carboxylic acid can comprise, consist essentially of, or consist of, an aliphatic carboxylic acid, an aromatic carboxylic acid, or any combination thereof; alternatively, an aliphatic carboxylic acid; or alternatively, an aromatic carboxylic acid. In some embodiments, the carboxylic acid can comprise, consist essentially of, or consist of, acetic acid, propionic acid, a butyric acid, a hexanoic acid, a heptanoic acid, an octanoic acid, a nonanoic acid, a decanoic acid, or any combination thereof; alternatively, propionic acid, a butyric acid, a hexanoic acid, a heptanoic acid, an octanoic acid, or any combination thereof. In other embodiments, the carboxylic acid can comprise, consist essentially of, or consist of, propionic acid, 1-butyric acid, 2-methylpropionic aid, 1-pentanoic acid, 3-methylbutanoic acid, trimethylacetic acid, 1-hexanoic acid, 2-ethylbutanoic acid, 1-heptanoic acid, 1-octanoic acid, 2-ethyl hexanoic acid, 1-decanoic acid, 1-dodecanoic acid, benzoic acid, succinic acid, or any combination thereof; alternatively, 1-hexanoic acid, 2-ethylbutanoic acid, 1-heptanoic acid, 1-octanoic acid, 2-ethyl hexanoic acid, or any combination thereof; alternatively, propionic acid; alternatively, 1-butyric acid; alternatively, 2-methylpropionic acid; alternatively, 1-pentanoic acid; alternatively, 3-methylbutanoic acid; alternatively, trimethylacetic acid; alternatively, 1-hexanoic acid; alternatively, 2-ethylbutanoic acid; alternatively, 1-heptanoic acid; alternatively, 1-octanoic acid; alternatively, 2-ethyl hexanoic acid; alternatively, 1-decanoic acid; alternatively, 1-dodecanoic acid; alternatively, benzoic acid; or alternatively, succinic acid.

Generally, in any aspect or embodiment where a carboxylic acid is utilized as the promoter, the carboxylic acid group to aluminum halide molar ratio can be any ratio which can provide a more desirable rate of formation of the oligomer product (or rate of monomer oligomerization) when compared to the rate in the absence of the carboxylic acid promoter and/or can provide a more desirable oligomer distribution when compared to the oligomer distribution in the absence of the carboxylic acid promoter. In an embodiment, the minimum carboxylic acid group to aluminum halide molar ratio can be $1 \times 10^{-3}:1$, $5 \times 10^{-3}:1$, $1 \times 10^{-2}:1$, $5 \times 10^{-2}:1$, $1 \times 10^{-1}:1$, or $5 \times 10^{-1}:1$. In an embodiment, the maximum carboxylic acid group to aluminum molar ratio can be 1.5:1, 1.2:1, 1.1:1, 1:1, $9 \times 10^{-1}:1$, $8 \times 10^{-1}:1$, $7 \times 10^{-1}:1$, $6 \times 10^{-1}:1$, or $5 \times 10^{-1}:1$. In an embodiment, the carboxylic acid group to aluminum halide molar ratio can range from any minimum carboxylic acid group to aluminum halide molar ratio described herein to any maximum carboxylic acid group to aluminum halide molar ratio described herein. Suitable ranges for the carboxylic acid group to aluminum halide molar ratio can include, but are not limited to, from $1 \times 10^{-1}:1$ to 1.5:1, from $1 \times 10^{-2}:1$ to 1.2:1, from $1 \times 10^{-1}:1$ to 1.1:1, from $1 \times 10^{-1}:1$ to 1:1, or from $5 \times 10^{-1}:1$ to 1:1. Other suitable carboxylic acid group to aluminum halide molar ratio ranges are readily apparent from the present disclosure.

In an embodiment, the ester that can be utilized as the promoter in any embodiment or aspect of the processes described herein can comprise, consist essentially of, or consist of, a $C_2$ to $C_{20}$ ester; a $C_2$ to $C_{15}$ ester; alternatively, a $C_3$ to $C_{10}$ ester; or alternatively, a $C_3$ to $C_8$ ester. In some embodiments, the ester can comprise, consist essentially of, or consist of, a mono-ester, a polyester, or any combination thereof; alternatively, a mono-ester, a di-ester, or any combination thereof; alternatively, a mono-ester; alternatively, a polyester; or alternatively, a di-ester. In some embodiments, the ester can comprise, consist essentially of, or consist of, a linear ester, a branched ester, or any combination thereof; alternatively, a linear ester; or alternatively a branched ester. In some embodiments, the ester can be an acyclic ester, a cyclic ester, or any combination thereof; alternatively, an acyclic ester; or alternatively, a cyclic ester. In other embodiments, the ester can comprise, consist essentially of, or consist of, an aliphatic ester, an aromatic ester, or any combination thereof; alternatively, an aliphatic ester; or alternatively, an aromatic ester. Generally, the esters which can be utilized as the promoter can be any ester which can be formed from any alcohol described herein as a potential promoter and any carboxylic acid described herein as a potential promoter. In some embodiments, the ester promoter can comprise, consist essentially of, or consist of, a methyl carboxylate, a ethyl carboxylate, a propyl carboxylate, a butyl carboxylate, a pentyl carboxylate, a hexyl carboxylate, or any combination thereof; or alternatively, a methyl carboxylate, a ethyl carboxylate, a 1-propyl carboxylate, a 2-propyl carboxylate, a 1-butyl carboxylate, 1,1-dimethyl-1-ethyl carboxylate (a tert-butyl carboxylate), a 1-pentyl carboxylate, a 1-hexyl carboxylate, or any combination thereof. In other embodiments, the ester which can be utilized as the promoter can be an acetate of any alcohol described herein as a promoter. Thus, in some embodiments, ester promoter can comprise, consist essentially of, or consist of, methyl acetate, ethyl acetate, a propyl acetate, a butyl acetate, a pentyl acetate, a hexyl acetate, or any combination thereof; alternatively, methyl acetate, ethyl acetate, 1-propyl acetate, 2-propyl acetate, 1-butyl acetate, 1,1-dimethyl-1-ethyl acetate (tert-butyl acetate), 1-pentyl acetate, 1-hexyl acetate, or any combination thereof; alternatively, methyl acetate; alternatively, ethyl acetate; alternatively, 1-propyl acetate; alternatively, 2-propyl acetate; alternatively, 1-butyl acetate; alternatively, 1,1-dimethyl-1-ethyl acetate (tert-butyl acetate); alternatively, 1-pentyl acetate; or alternatively, 1-hexyl acetate. Other suitable esters which can be utilized as the promoter are readily apparent by producing esters from the alcohol promoters and carboxylic acid promoter described in the present disclosure.

Generally, in any aspect or embodiment where an ester is utilized as the promoter, the ester group to aluminum halide molar ratio can be any ratio which can provide a more desirable rate of formation of the oligomer product (or rate of monomer oligomerization) when compared to the rate in the absence of the ester promoter and/or can provide a more desirable oligomer distribution when compared to the oligomer distribution in the absence of the ester promoter. In an embodiment, the minimum ester group to aluminum halide molar ratio can be $5 \times 10^{-2}:1$, $1 \times 10^{-1}:1$, $2.5 \times 10^{-1}:1$, $5 \times 10^{-2}:1$, $7.5 \times 10^{-1}:1$, or 1:1. In an embodiment, the maximum ester group to aluminum molar ratio can be 2:1, 1.5:1, 1.25:1, 1.1:1, 1:1, $9 \times 10^{-1}:1$, $8 \times 10^{-1}:1$, $7 \times 10^{-1}:1$, $6 \times 10^{-1}:1$, or $5 \times 10^{-1}:1$. In an embodiment, the ester group to aluminum halide molar ratio can range from any minimum ester group to aluminum halide molar ratio described herein to any maximum ester group to aluminum halide molar ratio described herein. Suitable ranges for the ester group to aluminum halide molar ratio can include, but are not limited to, from $5\times10^{-2}$:1 to 2:1, from $1\times10^{-1}$:1 to 1.5:1, from $7.5\times10^{-1}$:1 to 1.1:1, from $1\times10^{-1}$:1 to $8\times10^{-1}$:1, or from $1\times10^{-1}$:1 to $5\times10^{-1}$:1. Other suitable ester group to aluminum halide molar ratio ranges are readily apparent from the present disclosure.

In an embodiment, the ketone that can be utilized as the promoter in any embodiment or aspect of the processes described herein can comprise, consist essentially of, or consist of, a $C_3$ to $C_{20}$ ketone; a $C_3$ to $C_{15}$ ketone; alternatively, a $C_3$ to $C_{10}$ ketone; or alternatively, a $C_3$ to $C_8$ ketone. In some embodiments, the ketone can comprise, consist essentially of, or consist of, a monoketone, a polyketone, or any combination thereof; alternatively, a monoketone, a diketone, or any combination thereof; alternatively, a monoketone; alternatively, a polyketone, or alternatively, a diketone. In some embodiments, the ketone can comprise, consist essentially of, or consist of, a linear ketone, a branched ketone, or any combination thereof; alternatively, a linear ketone; or alternatively a branched ketone. In some embodiments, the ketone can be an acyclic ketone, a cyclic ketone, or any combination thereof; alternatively, an acyclic ketone; or alternatively, a cyclic ketone. In other embodiments, the ketone can comprise, consist essentially of, or consist of, an aliphatic ketone, an aromatic ketone, or any combination thereof; alternatively, an aliphatic ketone; or alternatively, an aromatic ketone. In some embodiments, the ketone promoter can comprise, consist essentially of, or consist of, acetone, 2-butanone, a pentanone, a hexanone, a heptanone, an octanone, or any combination thereof; alternatively, acetone, 2-butanone, 2-pentanone, 3-pentanone, 2-hexanone, 3-hexanone, 3-heptanone, or any combination thereof; alternatively, acetone; alternatively, 2-butanone; alternatively, 2-pentanone; alternatively, 3-pentanone; alternatively, 2-hexanone; alternatively, 3-hexanone; or alternatively, 3-heptanone.

Generally, in any aspect or embodiment where a ketone is utilized as the promoter, the carbonyl group to aluminum halide molar ratio can be any ratio which can provide a more desirable rate of formation of the oligomer product (or rate of monomer oligomerization) when compared to the rate in the absence of the ketone promoter and/or can provide a more desirable oligomer distribution when compared to the oligomer distribution in the absence of the ketone promoter. In an embodiment, the minimum carbonyl group to aluminum halide molar ratio can be $1\times10^{-3}$:1, $5\times10^{-3}$:1, $1\times10^{-2}$:1, $5\times10^{-2}$:1, or $1\times10^{-1}$:1. In an embodiment, the maximum carbonyl group to aluminum molar ratio can be 1.5:1, 1.2:1, 1.1:1, 1:1, $9\times10^{-1}$:1, $8\times10^{-1}$:1, $7\times10^{-1}$:1, $6\times10^{-1}$:1, or $5\times10^{-1}$:1. In an embodiment, the carbonyl group to aluminum halide molar ratio can range from any minimum carbonyl group to aluminum halide molar ratio described herein to any maximum carbonyl group to aluminum halide molar ratio described herein. Suitable ranges for the carbonyl group to aluminum halide molar ratio can include, but are not limited to, from $1\times10^{-3}$:1 to 1.5:1, from $1\times10^{-2}$:1 to 1.2:1, from $5\times10^{-2}$:1 to 1.2:1, from $1\times10^{-1}$:1 to 1.2:1, from $1\times10^{-1}$:1:1 to 1.1:1, or from $5\times10^{-2}$:1 to $5\times10^{-1}$:1. Other suitable carbonyl group to aluminum halide molar ratio ranges are readily apparent from the present disclosure.

In an embodiment, the ether that can be utilized as the promoter in any embodiment or aspect of the processes described herein can comprise, consist essentially of, or consist of, a $C_2$ to $C_{20}$ ether; a $C_3$ to $C_{15}$ ether; alternatively, a $C_3$ to $C_{10}$ ether; or alternatively, a $C_3$ to $C_8$ ether. In some embodiments, the ether can comprise, consist essentially of, or consist of, a monoether, a polyether, or any combination thereof; alternatively, a monoether, a diether, or any combination thereof; alternatively, a monoether; alternatively, a polyether, or alternatively, a diether. In some embodiments, the ether that can be utilized as the promoter can comprise, consist essentially of, or consist of, an acyclic ether, a cyclic ether, or any combination thereof; alternatively, an acyclic ether; or alternatively, a cyclic ether. In other embodiments, the ether that can be utilized as the promoter can comprise, consist essentially of, or consist of, an aliphatic ether, an aromatic ether, or any combination thereof; alternatively, an aliphatic ether; or alternatively, an aromatic ether. In some embodiments, the ether that can be utilized as the promoter can comprise, consist essentially of, or consist of, a linear ether, a branched ether, or any combination thereof; alternatively, a linear ether; or alternatively a branched ether. In yet further embodiments and independent of whether the ether promoter is saturated or olefinic, or acyclic or cyclic, the ether can that can be utilized as the promoter can comprise, consist essentially of, or consist of, a primary ether, a secondary ether, a tertiary ether, or any combination thereof; alternatively, a primary ether; alternatively, a secondary ether; or alternatively, a tertiary ether. It should be noted that a primary ether is an ether wherein each ether oxygen atom is attached to carbon atoms attached to zero or only one other non-monovalent atom, a secondary ether is an ether wherein at least one ether oxygen atom is attached to at least one carbon atom attached to only two other non-monovalent atoms, and a tertiary ether is an ether wherein at least one ether oxygen atom is attached to at least one carbon atom attached to three other non-monovalent atoms. In some embodiments, the ether can comprise, consist essentially of, or consist of, dimethyl ether, ethylmethyl ether, diethyl ether, ethylene glycol dimethyl ether, ethylene glycol methylethyl ether, ethylene glycol diethyl ether, propanediol dimethyl ether, propanediol methylethyl ether, propanediol diethyl ether, butanediol dimethyl ether, butanediol methylethyl ether, butanediol diethyl ether, diethylene glycol dimethyl ether, diethylene glycol methylethyl ether, diethylene glycol diethyl ether, triethylene glycol dimethyl ether, triethylene glycol methylethyl ether, triethylene glycol diethyl ether, pentaerythritol tetramethyl ether, or any combination thereof.

Generally, in any aspect or embodiment where an ether is utilized as the promoter, the ether oxygen to aluminum halide molar ratio can be any ratio which can provide a more desirable rate of formation of the oligomer product (or rate of monomer oligomerization) when compared to the rate in the absence of the ether promoter and/or can provide a more desirable oligomer distribution when compared to the oligomer distribution in the absence of the ether promoter. In an embodiment, the minimum ether oxygen to aluminum halide molar ratio can be $5\times10^{-2}$:1, $1\times10^{-1}$:1, $2.5\times10^{-1}$:1, $5\times10^{-1}$:1, or $7.5\times10^{-1}$:1. In an embodiment, the maximum ether oxygen to aluminum molar ratio can be 5:1 4:1 3:1, 2:1 or 1.5:1. In an embodiment, the ether oxygen to aluminum halide molar ratio can range from any minimum ether oxygen to aluminum halide molar ratio described herein to any maximum ether oxygen to aluminum halide molar ratio described herein. Suitable ranges for the ether oxygen to aluminum halide molar ratio can include, but are not limited to, $5\times10^{-2}$:1 to 5:1, from $1\times10^{-1}$:1 to 5:1, from $2.5\times10^{-1}$:1 to 5:1, from $5\times10^{-1}$:1 to 2:1, from $5\times10^{-1}$:1 to 2:1, from $7.5\times10^{-1}$:1 to 2:1:1, or from $7.5\times10^{-1}$:1 to 1.5:1. Other suitable ether oxygen to aluminum halide molar ratio ranges are readily apparent from the present disclosure.

In an embodiment, the halogenated hydrocarbon that can be utilized as the promoter in any embodiment or aspect of the processes described herein can comprise, consist essentially of, or consist of, a $C_1$ to $C_{24}$ halogenated hydrocarbon; a $C_1$ to $C_{20}$ halogenated hydrocarbon; alternatively, a $C_1$ to $C_{15}$ halogenated hydrocarbon; or alternatively, a $C_1$ to $C_{10}$ halogenated hydrocarbon. In an embodiment, the halogenated hydrocarbon promoter can be a hydrocarbon chloride, a hydrocarbon bromide, a hydrocarbon iodide, or any combination thereof; alternatively, a hydrocarbon chloride; alternatively, a hydrocarbon bromide; or alternatively, a hydrocarbon iodide. In an embodiment, the halogenated hydrocarbon promoter can comprise at least one carbon atom having only one attached halogen atom. In some embodiments, the halogenated hydrocarbon promoter can be an acyclic halogenated hydrocarbon, a cyclic halogenated hydrocarbon, or any combination thereof; alternatively, an acyclic halogenated hydrocarbon; or alternatively, a cyclic halogenated hydrocarbon. In other embodiments, the halogenated hydrocarbon promoter can comprise, consist essentially of, or consist of, an aliphatic halogenated hydrocarbon, an aromatic halogenated hydrocarbon, or any combination thereof; alternatively, an aliphatic halogenated hydrocarbon; or alternatively, an aromatic halogenated hydrocarbon. In further embodiments, the halogenated hydrocarbon promoter can comprise, consist essentially of, or consist of, a saturated halogenated hydrocarbon, an olefinic halogenated hydrocarbon. In some embodiments, the halogenated hydrocarbon promoter can comprise, consist essentially of, or consist of, a linear halogenated hydrocarbon, a branched halogenated hydrocarbon, or any combination thereof; alternatively, a linear halogenated hydrocarbon; or alternatively a branched halogenated hydrocarbon. In yet further embodiments and independent of whether the halogenated hydrocarbon promoter is saturated or olefinic, or acyclic or cyclic, the halogenated hydrocarbon promoter can comprise, consist essentially of, or consist of, a primary halogenated hydrocarbon, a secondary halogenated hydrocarbon, a tertiary halogenated hydrocarbon, or any combination thereof; alternatively, a primary halogenated hydrocarbon; alternatively, a secondary halogenated hydrocarbon; or alternatively, a tertiary halogenated hydrocarbon.

In an embodiment, the halogenated hydrocarbon which can be utilized as a promoter can comprise, consist essentially of, or consist of, a methyl halide, a ethane halide, a propyl halide, a butyl halide, a pentyl halide, a hexyl halide, a heptyl halide, an octyl halide, a nonyl halide, a decyl halide, or any combination thereof; alternatively, a halomethane, a haloethane, a 1-halo-propane, a 2-halopropane, a 1-halobutane, a 2-halobutane, a 1-halo-2-methylpropane, a 2-halo-2-methyl propane, a 1-halopentane, a 1-halohexane, or any combination thereof. In some embodiments, the halogenated hydrocarbon which can be utilized as a promoter can comprise, consist essentially of, or consist of, a cyclopentane halide or a cyclohexane halide; alternatively, a cyclopentane halide; or alternatively, a cyclohexane halide. In other embodiments, the halogenated hydrocarbon which can be utilized as a promoter can comprise, consist essentially of, or consist of, an allyl halide, a benzyl halide, or any combination thereof; alternatively, an allyl halide; or alternatively, a benzyl halide. Generally, the halide of any hydrocarbon halide (or halohydrcarbon) which can be utilized as a promoter described herein can be a hydrocarbon chloride (or a chlorohydrocarbon), a hydrocarbon bromide (or a bromohydrocarbon), a hydrocarbon iodide (or a iodohydrocarbon), or any combination thereof; alternatively, hydrocarbon chloride (or a chlorohydrocarbon); alternatively, a hydrocarbon bromide (or a bromohydrocarbon); or alternatively, a hydrocarbon iodide (or a iodohydrocarbon). Exemplary hydrocarbon halides which can be utilized as a promoter include, but are not limited to methyl chloride, methyl bromide, methyl iodide, ethyl chloride, ethyl bromide, ethyl iodide, 1,2-dichloroethane, 1,2-dibromoethane 1-chloropropane, 1-bromopropane, 2-chloropropane, 2-bromopropane, allyl chloride, allyl bromide, allyl iodide, tert-butyl chloride, tert-butyl bromide, tert-butyl iodide, cyclohexyl chloride, cyclohexyl bromide, benzyl chloride, benzyl bromide, benzyl bromide, or combination thereof.

Generally, in any aspect or embodiment where a halogenated hydrocarbon is utilized as the promoter, the halogen to aluminum halide molar ratio can be any ratio which can provide a more desirable rate of formation of the oligomer product (or rate of monomer oligomerization) when compared to the rate in the absence of the halogenated hydrocarbon promoter and/or can provide a more desirable oligomer distribution when compared to the oligomer distribution in the absence of the halogenated hydrocarbon promoter. In an embodiment, the minimum halogen to aluminum halide molar ratio can be $5\times10^{-2}$:1, $1\times10^{-1}$:1, $2.5\times10^{-1}$:1, $5\times10^{-1}$:1, or $7.5\times10^{-1}$:1. In an embodiment, the maximum halogen to aluminum molar ratio can be 10:1, 5:1, 4:1, 3:1, 2:1 or 1.5:1. In an embodiment, the halogen to aluminum halide molar ratio can range from any minimum halogen to aluminum halide molar ratio described herein to any maximum halogen to aluminum halide molar ratio described herein. Suitable ranges for the halogen to aluminum halide molar ratio can include, but are not limited to, $5\times10^2$:1 to 10:1, from $1\times10^{-1}$:1 to 10:1, from $2.5\times10^{-1}$:1 to 5:1, from $5\times10^{-1}$:1 to 2:1, from $5\times10^{-1}$:1 to 1.5:1, from $7.5\times10^{-1}$:1 to 2:1 or from $7.5\times10^{-1}$:1 to 1.5:1. Other suitable halogen to aluminum halide molar ratio ranges are readily apparent from the present disclosure.

When a promoter is utilized, the promoter can be introduced as a component of the catalyst mixture; alternatively, can be introduced with the monomer; or alternatively, can be introduced as a separate component to the processes described herein.

In any aspect or embodiment disclosed herein, a metal halide (other than the aluminum halide component utilized as a catalyst, component of the catalyst mixture, or catalyst system mixture), an alkyl metal halide (other than the alkyl aluminum halide component utilized as a catalyst, component of the catalyst mixture, or catalyst system mixture), an alkyl metal compound, or any combination thereof can be utilized in any process including the formation of an oligomer product; alternatively, a metal halide (other than the aluminum halide and/or the aluminum trihalide component which can be utilized as a catalyst, component of the catalyst mixture, or catalyst system mixture) can be utilized in any process including the formation of an oligomer product; alternatively, an alkyl metal halide (other than an alkyl aluminum halide component which can be utilized as a catalyst, component of the catalyst mixture, or catalyst system mixture) can be utilized in any process including the formation of an oligomer product; or alternatively, an alkyl metal compound can be utilized in any process including the formation of an oligomer product. In an embodiment, the metal halide, the alkyl metal halide, and/or the alkyl metal compound can be a component of the catalyst mixture (or catalyst system mixture); or alternatively, the metal halide, the alkyl metal halide, and/or the alkyl metal compound can be contacted with the catalyst (or catalyst mixture, or catalyst system mixture) and monomer to form the oligomer product. Generally, the metal halide can be any compound which can increase the rate of formation of the oligomer product (or rate of monomer oligomerization) when compared to the rate in the absence of the metal halide and/or can provide a more desirable oligomer distribution when compared to the oligomer distribution in the absence of the metal halide.

In an embodiment, the metal of the metal halide, alkyl metal halide, and/or the alkyl metal compound can be a Group 4-10 metal; alternatively, a Group 4-8 metal; or alternatively, a Group 4-5 metal. In some embodiments the metal of the metal halide, alkyl metal halide, and/or the alkyl metal compound can be titanium, vanadium, zirconium, chromium, or iron; alternatively, titanium, vanadium, or iron; alternatively, titanium; alternatively, vanadium; or alternatively, iron. In an embodiment, each halide of the metal halide and/or alkyl metal halide independently can be chloride, bromide, or iodide; alternatively, chloride; alternatively, bromide; or alternatively, iodide. In an embodiment, each alkyl group of the alkyl metal halide and/or the alkyl metal compound can be a methyl group, an ethyl group, a propyl group, a butyl group, a pentyl group, a hexyl group, or a heptyl group; alternatively, an ethyl group, an n-butyl group, an iso-butyl group or a hexyl group; alternatively, an ethyl group; alternatively, a n-butyl group; or alternatively, an iso-butyl group. In some embodiments, the metal halide can comprise, consist essentially of, or consist of, titanium trichloride, titanium tetrachloride, vanadium trichloride, vanadium tetrachloride, iron dichloride, or iron trichloride; alternatively, titanium tetrachloride, vanadium tetrachloride, or iron trichloride; or alternatively, titanium tetrachloride. In embodiments where the catalyst is aluminum trihalide (as a component of a catalyst mixture or otherwise), the alkyl metal halide can be alkyl aluminum halide having the formula $R_yAlX_{3-y}$ wherein y can range from greater than 0 to less than 3. Alkyl aluminum halides having the formula $R_yAlX_{3-y}$ wherein y can range from greater than 0 to less than 3 (general and specific) are described herein as potential selections for the catalyst and this alkyl aluminum halide can be utilized, without limitation, as the alkyl metal halide when the catalyst is aluminum trihalide (as a component of a catalyst mixture or otherwise). In some embodiments, the alkyl metal compound can be a trialkylaluminum compound. Alkyl groups for the alkyl metal compound are described herein and these can be utilized, without limitation, to further describe the trialkylaluminum compound. In some embodiments, the trialkylaluminum compound can comprise, consist essentially, or consist of, triethylaluminum, tributylaluminum, trihexylaluminum, trioctylaluminum, or any combination thereof; alternatively triethylaluminum, tri-n-butylaluminum, tri-iso-butylaluminum, or any combination thereof; alternatively, triethyl aluminum; or alternatively, tri-iso-butylaluminum.

Generally, in any aspect or embodiment where a metal halide, alkyl metal halide, and/or the alkyl metal compound is utilized in conjunction with the aluminum halide catalyst, the metal of the metal halide, alkyl metal halide, and/or the alkyl metal compound to aluminum halide molar ratio (metal to aluminum molar ratio) can be any metal to aluminum molar ratio which can provide a more desirable rate of formation of the oligomer product (or rate of monomer oligomerization) when compared to the rate in the metal halide, alkyl metal halide, and/or the alkyl metal compound and/or can provide a more desirable oligomer distribution when compared to the oligomer distribution in the absence of the metal halide, alkyl metal halide, and/or the alkyl metal compound. In an embodiment, the minimum metal to aluminum molar ratio can be $1\times10^{-1}:1$, $2.5\times10^{-1}:1$, $5\times10^{-1}:1$, $7.5\times10^{-2}:1$, or 1:1. In an embodiment, the maximum metal to aluminum molar ratio can be 3:1, 2.5:1, 2:1, 1.5:1, 1.25:1, 1.1:1 or 1:1. In an embodiment, the hydroxy group to aluminum halide molar ratio can range from any minimum metal to aluminum molar ratio described herein to any maximum metal to aluminum molar ratio described herein. Suitable ranges for the metal to aluminum molar ratio can include, but are not limited to, from $1\times10^{-1}:1$ to 3:1, from $2.5\times10^{-1}:1$ to 2.5:1, from $5\times10^{-1}:1$ to 2:1, from $5\times10^{-1}:1$ to 1.5:1, or from $5\times10^{-1}:1$ to 1.25:1. Other suitable metal to aluminum molar ratio ranges are readily apparent from the present disclosure.

The processes to produce oligomer product and/or polyalphaolefins disclosed herein can be either continuous or batch. However, as noted herein, the process to form the oligomer product can be conducted in the presence of, or the substantial absence of, an organic solvent. In an aspect, the monomer can be added to the catalyst and/or to the catalyst mixture; alternatively, the catalyst and/or the catalyst mixture can be added to the monomer; or alternatively, the catalyst and/or catalyst mixture and the monomer can be simultaneously introduced into a reaction zone.

Some of the processes to produce oligomer product and/or polyalphaolefins disclosed herein can be continuous processes. In an embodiment, the process to produce oligomer product can comprise the introduction of a monomer and catalyst (and/or a catalyst mixture) into a reaction zone and withdrawing from the reaction zone a reaction effluent comprising an oligomer product.

The reaction zone of the process can be defined by any reaction means known in the art that provide conditions to form the oligomer product. The reaction zone can be a reactor vessel into which the monomer, the catalyst (and/or the catalyst mixture), and/or any other components (e.g., promoter, among other components described herein) can be introduced. The monomer, the catalyst (and/or the catalyst mixture), and/or any other components (e.g., promoter, among other components described herein) can be introduced separately into the reaction zone as separate feed streams, or they can be introduced together as a premixed mixture. A suitable reaction zone can be compatible with a continuous, semi-continuous, or batch process. One type of reactor that can be utilized is a continuous stirred tank reactor (CSTR).

The conditions capable of forming an oligomer product within the reaction zone can be maintained to provide the dimerization, oligomerization or polymerization, or any combination thereof of the monomer to form an oligomer product. In an embodiment, the conditions capable of forming an oligomer product can comprise a temperature, a pressure, a time, or any combination thereof; alternatively, a temperature and a pressure; alternatively, a temperature and a time; or alternatively, a temperature, a pressure and a time.

Generally, the pressure which can be utilized as a condition capable of forming an oligomer product can be any pressure which can facilitate the formation of the oligomer product. In an embodiment, the minimum pressure which can be utilized as a condition capable of forming the oligomer product can be 7.4 psia (51 kPa), 11 psia (76 kPa), 14.7 psia (101 kPa), 21 psia (145 kPa), 30 psia (207 kPa), or 50 psia (345 kPa). In an embodiment, the maximum pressure which can be utilized as a condition capable of forming the oligomer product can be 1000 psia (6.9 Mpa), 750 psia (5.2 MPa), 500 psia (3.4 MPa), 250 psia (1.7 MPa), 100 psia (689 kPa), 75 psia (517 kPa), or 50 psia (345 kPa). In an embodiment, the pressure which can be utilized as a condition capable of forming the oligomer product can range from any minimum pressure which can be utilized as a condition capable of forming the oligomer product to any maximum pressure which can be utilized as a condition capable of forming the oligomer product described herein. In some embodiments, suitable ranges for the pressure which can be utilized as a condition capable of forming the oligomer product can include, but are not limited to, from 7.4 psia (51 kPa) to 1000 psia (6.9 Mpa), from 11 psia (76 kPa) to 250 psia (1.7 MPa), from 14.7 psia (101 kPa) to 100 psia (689 kPa), from 14.7 psia (101 kPa) to 50 psia (345 kPa). Other suitable pressure ranges which can be utilized as a condition capable of forming the oligomer product are readily apparent from the present disclosure.

Generally, the temperature which can be utilized as a condition capable of forming an oligomer product can be any pressure which can facilitate the formation of the oligomer product. In an embodiment, the minimum temperature which can be utilized as a condition capable of forming the oligomer product can be 0° C., 25° C., 40° C., 60° C., or 80° C. In an embodiment, the maximum temperature which can be utilized as a condition capable of forming the oligomer product can be 200° C., 175° C., 150° C., 135° C., 120° C., or 100° C. In an embodiment, the temperature which can be utilized as a condition capable of forming the oligomer product can range from any minimum temperature which can be utilized as a condition capable of forming the oligomer product to any maximum temperature which can be utilized as a condition capable of forming the oligomer product described herein. In some embodiments, suitable ranges for the temperature which can be utilized as a condition capable of forming the oligomer product can include, but are not limited to, from 0° C. to 200° C., from 25° C. to 175° C., from 40° C. to 150° C., from 60° C. to 140° C., from 80° C. to 140° C., from 60° C. to 120° C., or from 80° C. to 100° C. Other suitable temperature ranges which can be utilized as a condition capable of forming the oligomer product are readily apparent from the present disclosure.

Generally, the time over which the oligomer product is formed as a condition capable of forming an oligomer product can be any time which can provide the monomer conversion and/or desired oligomer distribution. In relation to continuous processes, the time over which the oligomer product is formed as a condition capable of forming an oligomer product can be the ratio of the reactor zone volume to the volumetric introduction rate of any of the feeds, (e.g., the monomer, the catalyst (or the catalyst mixture), and any other components (e.g., promoter, among other components described herein)) charged to or introduced into the reaction zone. The time is in units of time. It should be noted that in some situations the time can be the average amount of time the particular materials (e.g., the monomer, the catalyst (or the catalyst mixture), and any other components (e.g., promoter, among other components described herein), among others) spend within the reaction zone. The minimum time (or minimum average time) can be 1 minute, 2 minutes, 5 minutes, 10 minutes, or 15 minutes. The maximum time (or average maximum time) can be 600 minutes, 500 minutes, 400 minutes, 300 minutes, 200 minute or 150 minutes. In an embodiment, the time (or average time) which can be utilized as a condition capable of forming the oligomer product can range from any minimum time (or average minimum time) which can be utilized as a condition capable of forming the oligomer product to any maximum time (or average maximum time) which can be utilized as a condition capable of forming the oligomer product described herein. In some embodiments, the time (or average time) which can be utilized as a condition capable of forming the oligomer product can range, but is not limited to, from 1 minute to 600 minutes, from 2 minutes to about 500 minutes, from 5 minutes to 400 minutes, from 10 to 400 minutes, or from 10 to 300 minutes. Other suitable time ranges (or average time ranges) which can be utilized as a condition capable of forming the oligomer product are readily apparent from the present disclosure.

Generally, any of the processes described herein can be operated to convert any desired quantity of the monomer to an oligomer product and/or produce an oligomer product having any desired oligomer distribution. In an embodiment, at least 50 mole %, 60 mole %, 70 mole %, 75 mole %, 80 mole %, 85 mole %, 90 mole %, or 95 mole % of the monomer can be converted to an oligomer product. In an embodiment, the processes described herein can be operated to produce an oligomer product comprising dimers, trimers, and/or higher oligomer products. In some embodiments, the oligomer product can comprise at least 50 wt. %, 60 wt. %, 65 wt. %, 70 wt. %, 75 wt. %, 80 wt. % or 85 wt. % trimers plus higher oligomers. In some embodiments, the oligomer product can comprise a maximum of 40 wt. %, 35 wt. %, 30 wt. %, 25 wt. %, 20 wt. %, or 15 wt. % dimers. The wt. % of the dimers, trimer, and higher oligomer products is based upon the total weight of the oligomer product.

In an embodiment, the processes disclosed herein can include a step of separating the oligomer product (or a portion of the oligomer product) from the monomer; alternatively, the monomer and organic diluent (if utilized), to yield a separated oligomer product. In some embodiments, the catalyst (or catalyst system) can be deactivated prior to separating the oligomer product (or a portion of the oligomer product) from the monomer (or the monomer and organic diluent). In other embodiments, the catalyst (or catalyst system) can be separated from the oligomer product (or a portion of the oligomer product) during the separation of the oligomer product (or a portion of the oligomer product) from the monomer (or the monomer and organic diluent). In an embodiment, the processes disclosed herein can include a step of separating the oligomer product (or a portion of the oligomer product) from the organic liquid carrier. It should be noted that a portion of the organic liquid carrier can react either with itself or with the monomer to form oligomer product. Once contacted with the monomer, any organic liquid carrier olefins in a catalyst mixture (or catalyst system mixture) which reacts to form oligomer product may be considered part of the oligomer product. Consequently, all of the organic liquid carrier may not be recovered in the separation of the oligomer product from the organic liquid carrier. In some embodiments, the separating of the oligomer product (or a portion of the organic liquid carrier) from the monomer can also serve to separate the oligomer product (or portion of the oligomer product) from the organic liquid carrier. It should further be noted that the separation of oligomer product from the monomer or the organic liquid carrier may not be complete and the residual amounts of the monomer and/or organic liquid carrier can be present in the separated oligomer product.

Generally, the catalyst (or catalyst system) can be deactivated using any method or material which can deactivate the catalyst (or catalyst system) for converting the monomer to the oligomer product. In an embodiment, the deactivation of the catalyst (or catalyst system) can occur in the reactor in which the oligomer product is formed; or alternatively, a reactor effluent can be removed from the reactor in which the oligomer product is formed and the deactivation of the catalyst (or catalyst system) can occur in a vessel, transfer line, or reactor (among other choices) different from the reactor in which the oligomer product is formed. In an embodiment, the catalyst (or catalyst system) can be deactivated by contacting the reactor effluent with a catalyst deactivating agent comprising a solution comprising water and substantially devoid of a Group 1 or Group 2 metal hydroxide; or alternatively, a catalyst deactivating agent comprising an aqueous solution comprising a Group 1 and/or Group 2 metal hydroxide. As utilized herein, substantially devoid of a Group 1 or Group 2 metal hydroxide refers to a solution containing less than 500 ppm (by weight) of a Group 1 or Group 2 metal hydroxide. In an embodiment, the reactor effluent can comprise monomer, catalyst (or catalyst system), and oligomer product; or alternatively, monomer, catalyst (or catalyst system), oligomer product, and organic diluent. In an embodiment, the Group 1 metal hydroxide utilized in the aqueous solution of the Group 1 and/or Group 2 metal hydroxide can comprise, consist essentially of, or consist of lithium hydroxide, sodium hydroxide, potassium hydroxide, rubidium hydroxide, cesium hydroxide, or any combination thereof; alternatively, sodium hydroxide; alternatively, potassium hydroxide. In an embodiment, the Group 2 metal hydroxide utilized in the aqueous solution of the Group 1 and/or Group 2 metal hydroxide can comprise, consist essentially of, or consist of, beryllium hydroxide, magnesium hydroxide, calcium hydroxide, strontium hydroxide, or barium hydroxide, or any combination thereof; alternatively, magnesium hydroxide; or alternatively, calcium hydroxide. In some embodiments, after the reactor effluent is contacted with the aqueous solution comprising the Group 1 and/or Group 2 metal hydroxide), the organic layer/phase comprising the oligomer product (or comprising the oligomer product and monomer) can be separated from the aqueous layer/phase comprising the Group 1 and/or Group 2 metal hydroxide, to yield a separated organic layer/phase and a separated aqueous layer/phase. In some embodiments, the separated organic layer/phase can be washed with a solution comprising water and substantially devoid of a Group 1 or Group 2 metal hydroxide, and the organic layer/phase can then be separated from the aqueous layer/phase. In some embodiments, the solution comprising water and substantially devoid of a Group 1 and/or Group 2 metal hydroxide or the aqueous solution comprising a Group 1 and/or Group 2 metal hydroxide can contain one or more additional components which can facilitate the contacting of the aqueous solution and the reactor effluent and/or components which can facilitate the separation of the aqueous layer/phase from the organic layer/phase. Generally, the separated organic layer/phase can comprise monomer and oligomer product; or alternatively, monomer, oligomer product, and organic diluent.

In an embodiment, processes disclosed herein can include separating the oligomer product (or a portion of the oligomer product) from the separated organic phase, to yield a separated oligomer product. In other embodiments, processes disclosed herein can include separating the oligomer product (or a portion of the oligomer product) from the monomer, the catalyst (catalyst system; deactivated catalyst; or deactivated catalyst system), and the organic liquid carrier; alternatively, separating the oligomer product (or a portion of the oligomer product) from the monomer, organic diluent, the catalyst (catalyst system; deactivated catalyst; or deactivated catalyst system), and the organic liquid carrier. Further embodiments can include separating the monomer (or a portion of the monomer), the organic liquid carrier, and/or organic diluent (if utilized) and recycling the recovered monomer (or a portion of the monomer) and/or the recovered organic liquid diluent (or portion of the organic liquid carrier); or separating the monomer (or a portion of the monomer) and recycling the monomer (or the portion of the monomer). The separations can be performed using any known process. In some embodiments, one or more of the separating step(s) can be performed by distillation.

Following the separation of the oligomer product, the residual unsaturation in the oligomer product can be reduced by hydrogenating the oligomer product to form a polyalphaolefin. The hydrogenation can be accomplished by any means known to those with ordinary skill in the art. In an embodiment, all or a portion of the oligomer product can be separated from the monomer. In some embodiments, the oligomer product can be separated (either concurrently with the separation from the monomer or as a separation distinct from the separation from the monomer) into one or more fractions comprising, or consisting essentially of, trimers or higher oligomers. The separated oligomer product (all or a portion of) can be fed to a hydrogenation unit to hydrogenate unsaturated double bonds and produce a hydrogenated oligomer product, for example polyalphaolefins. In some embodiments, the separated oligomer product(s) can be stored prior to hydrogenation. In other embodiments, the polyalphaolefin can be separated into one or more fractions comprising, or consisting essentially of, hydrogenated trimer of higher hydrogenated oligomers.

In an embodiment, any oligomer product produced by the processes described herein can be hydrogenated by reaction with hydrogen gas to form a polyalphaolefin. Generally, the hydrogenation can comprise contacting the oligomer product (e.g., separated oligomer product) and a hydrogenation catalyst to form a polyalphaolefin under conditions capable of hydrogenating the oligomer product. In some embodiments, the oligomer product (e.g., separated oligomer product) can be hydrogenated to produce a polyalphaolefin having any bromine number or bromine index described herein.

In an embodiment, the hydrogenation catalyst can comprise, or consist essentially of, a supported Group 7, 8, 9, and 10 metals. In some embodiments, the hydrogenation catalyst can be selected from the group consisting of one or more of Ni, Pd, Pt, Co, Rh, Fe, Ru, Os, Cr, Mo, and W, supported on silica, alumina, clay, titania, zirconia, or a mixed metal oxide supports. In other embodiments, the hydrogenation catalyst can be nickel supported on kieselguhr, platinum or palladium supported on alumina, or cobalt-molybdenum supported on alumina; alternatively, nickel supported on kieselguhr; alternatively, platinum or palladium supported on alumina; or alternatively, cobalt-molybdenum supported on alumina. In yet other embodiments, the hydrogenation catalyst can be one or more of the group consisting of nickel supported on kieselguhr, silica, alumina, clay or silica-alumina.

Generally, the hydrogenation of the oligomer product to form a polyalphaolefin can be performed in any type of process and/or reactor which can hydrogenate the oligomer product to the desired bromine number or bromine index. In an embodiment, the hydrogenation of the oligomer product to form a polyalphaolefin can be performed in a batch process, a continuous process; or any combination thereof, alternatively a batch process; or alternatively a continuous process. In some embodiments, the hydrogenation of the oligomer product to form a polyalphaolefin can be performed in a slurry reactor, a continuous stirred tank reactor, a fixed bed reactor or any combination thereof; alternatively, a slurry reactor; alternatively, a continuous stirred tank reactor; or alternatively, a fixed bed reactor. Generally, the product polyalphaolefin can be filtered to separate the hydrogenation catalyst and/or catalyst fines from the polyalphaolefin. Further, the polyalphaolefin can be distilled to further purify the polyalphaolefin; alternatively, distilled to form two or more compositions comprising, or consisting essentially of, polyalphaolefins having different nominal viscosities; or alternatively, distilled to further purify the polyalphaolefin and form two or more compositions comprising, or consisting essentially of, polyalphaolefins having different nominal viscosities.

The quantity of hydrogenation catalyst utilized to hydrogenate the oligomer product (or portion of the oligomer product) (e.g., separated oligomer product) is dependent upon the identity of the hydrogenation catalyst and the particular hydrogenation process utilized. Generally, the amount of hydrogenation catalyst used can be any amount which can produce the desired polyalphaolefin bromine number (or bromine index) under the desired conditions capable of forming the polyalphaolefin. In a non-fixed bed hydrogenation process (e.g., slurry reactors or continuous stirred tank reactors, among others), the amount of hydrogenation catalyst used in the hydrogenation can range from 0.001 wt. % to 20 wt. %, 0.01 wt. % to 15 wt. %, 0.1 wt. % to 10 wt. %, or 1 wt. % to 5 wt. %. In a fixed bed processes, the WHSV (weight hourly space velocity) of the oligomer product or portion of oligomer product) over the hydrogenation catalyst can range from 0.01 to 10, 0.05 to 7.5, or 0.1 to 5. The wt. % of the hydrogenation catalyst is based upon the total weight of the hydrogenation catalyst and the oligomer product (or portion of oligomer product) being subjected to hydrogenation.

Generally, the conditions capable of hydrogenating the oligomer product (e.g., separated oligomer product) can comprise a hydrogen pressure, a temperature, a contact time, or any combination thereof; alternatively, a hydrogen pressure and a temperature; alternatively, a hydrogen pressure, a temperature, and a contact time. In an embodiment, the temperature of the hydrogenation that can be utilized as a condition capable of hydrogenating the oligomer product can range from 25° C. to 350° C., from 50° C. to 300° C., from 60° C. to 250° C., or from 70° C. to 200° C. In an embodiment, the hydrogen pressure that can be utilized as a condition capable of hydrogenating the oligomer product can range from 100 kPa to 10 MPa, 250 kPa to 7 MPa, 500 kPa to 5 MPa, or 750 kPa to 2 MPa. In an embodiment, the contact time that can be utilized as a condition capable of hydrogenating the oligomer product can range from 1 minutes to 100 hours, from 2 minutes to 50 hours, 5 minutes to 25 hour, or 10 minute to 10 hours. Additional information on the hydrogenation of olefin oligomers (e.g., olefin oligomer such as the oligomer product that can be produced by the processes described herein) to form polyalphaolefins can be found in U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY (1994).

In an embodiment, the polyalphaolefin can be subjected to processes to reduce the amount of heteroatom containing compounds to acceptable levels for the desired polyalphaolefin use. In some embodiments, the polyalphaolefin can contain a maximum of 600 ppm, 300 ppm, 100 ppm, 50 ppm, 10 ppm, 5 ppm, or 1 ppm of heteroatom containing compounds. In an embodiment, the heteroatomic compounds whose presence can be reduced in the polyalphaolefin can include halogen containing compounds such as organic and/or inorganic fluorides, chlorides, bromides, or iodides.

In an embodiment, any polyalphaolefin produced by a processes described herein can have a 100° C. kinematic viscosity from 1.5 cSt to 50 cSt; alternatively, from 1.5 cSt to 30 cSt; alternatively, from 1.5 cSt to 20 cSt; alternatively, from 1.5 cSt to 10 cSt. In other embodiments, any polyalphaolefin produced by a process described herein can have a 100° C. kinematic viscosity of about 2 cSt, about 2.5 cSt, about 4 cSt, about 5 cSt, about 6 cSt, about 7 cSt, about 8 cSt, or about 9 cSt. Generally, the kinematic viscosity can be measured using ASTM D445-12 or ASTM D7042-12a.

In an embodiment, any polyalphaolefin produced by a process described herein can have minimum viscosity index of 100, 110, 120, 130, 140 or 150. In other embodiments, any polyalphaolefin produced by a process described herein can have viscosity index ranging from 100 to 250, from 110 to 225, or from 120 to 200. The viscosity index is a measure of the variation in kinematic viscosity of a product due to changes in the temperature between 40° C. and 100° C. Generally, the viscosity index can be measured according to ASTM D2270-10e1.

In an embodiment, any polyalphaolefin produced by a process described herein can have a pour point less than or equal to −20° C., −30° C., −35° C., −40° C., −45° C., or −50° C. Any polyalphaolefin produced by a process described herein can have a pour point from −20° C. to −100° C., alternatively, from −25° C. to −95° C., alternatively, from −30° C. to −90° C.; or alternatively, from −35° C. to −85° C. Generally, the pour point can be measured using ASTM D97-12.

In an embodiment, any polyalphaolefin produced by a process described herein can have a maximum bromine number of 2, 1.8, 1.6, 1.4, 1.2, or 1 as determined by ASTM D1159-09 and has units of grams bromine per 100 grams of sample (g Br/100 g). In other embodiments, any polyalphaolefin produced by a process described herein can have a maximum bromine index of 1000, 800, 600, or 500 as determined by ASTM D2710-09 and has units of milligrams bromine per 100 grams of sample (mg Br/100 g).

In an aspect, the polyalphaolefin described herein can be further used in a variety of components or products for a diverse range of applications and industries. For example, the polyalphaolefins can be utilized as a lubricant base oil (or a component of a lubricant base oil) for lubricant compositions and/or functional fluid compositions. Exemplary lubricant compositions in which the polyalphaolefins produced by the processes described herein can be utilized include, but are not limited to, greases, gearbox oils, engine oils, transmission fluids, and/or drilling fluids. Exemplary functional fluid compositions in which the polyalphaolefins produced by the processes described herein can be utilized include, but are not limited to, hydraulic fluids, drilling fluids, coolant fluids, and/or dielectric coolant fluids. In an aspect, the polyalphaolefin produced by a processes described herein can be utilized as the sole Base Oil for a lubricant composition and/or functional fluid composition. In other aspects, the polyalphaolefin produced by a process described herein can be combined with one or more other Base Oils to form a Base Oil for a lubricant composition and/or functional fluid composition. In an embodiment, the polyalphaolefin produced by a processes described herein can be blended with a Group I Base Oil, Group II Base Oil, Group III Base Oil, another Group IV Base Oil, a Group V Base Oil, or any combination of thereof to form a lubricant base oil for lubricant compositions and/or functional fluid compositions. As utilized herein, the Base Oil groups are those as designated by The American Petroleum Institute (API). Additional information on the use of polyalphaolefin in lubricant compositions and/or functional fluid compositions can be found in "Synthetic Lubricants and High-Performance Functional Fluids," 2nd Ed., L. Rudnick, ed., Marcel Dekker, Inc., NY (1999). Additional information on additives used in product formulation can be found in "Lubricants and Lubrications," T. Mang and W. Dresel, eds., Wiley-VCH GmbH, Weinheim (2001).

Fully formulated lubricants can further include one or more additives. Additives which can be include in a fully formulated lubricant can include but are not limited to viscosity index improvers/viscosity modifiers/viscosity improver, dispersants (metallic and/or non-metallic), detergents (metallic and/or non-metallic), friction modifiers, traction improving additives, demulsifiers, defoamants, antioxidants, anti-wear additives (metallic and non-metallic, phosphorus-containing and non-phosphorus, sulfur-containing and non-sulfur types), extreme-pressure additives (metallic and non-metallic, phosphorus-containing and non-phosphorus, sulfur-containing and non-sulfur types), anti-rust additives, corrosion inhibitors, metal deactivators, anti-seizure agents, pour point depressants, wax modifiers, seal compatibility agents, friction modifiers, lubricity agents, anti-staining agents, chromophores (dyes), and/or haze inhibitors. Additional information on additives used in product formulations can be found in "Fuels and Lubricants Handbook: Technology, Properties, Performance, and Testing" edited by George E. Totten, Steven R. Westbrook, Rajesh J. Shah, ASTM (2003), ISBN 0-8031-2096-6; Chapter 9 Additives and Additive Chemistry, pp. 199-248, "Lubricants and Related Products," Klamann, Verlag Chemie, Deerfield Beach, Fla., ISBN 0-89573-177-0; "Lubricant Additives" by M. W. Ranney, published by Noyes Data Corporation of Parkridge, N.J. (1973); "Lubricants and Lubrications," T. Mang and W. Dresel, eds., Wiley-VCH GmbH, Weinheim (2001); and "Lubricant Additives", C. V. Smallheer and R. K. Smith, published by the Lezius-Hiles Co. of Cleveland, Ohio (1967).

Viscosity index improvers (also known as viscosity modifiers and viscosity improvers) can provide lubricant compositions and/or functional fluid compositions with high and low temperature operability. These additives can impart shear stability at elevated temperatures and acceptable viscosity at low temperatures. Suitable viscosity index improvers can include high molecular weight hydrocarbons, olefin polymers and copolymers, polyesters, and viscosity index improver dispersants that function as both a viscosity index improver and a dispersant. Viscosity index improvers can have molecular weights ranging from about 10,000 Da to about 1,000,000 Da, from about 20,000 Da to about 500,000 Da, or from about 50,000 Da to about 200,000 Da.

Viscosity index improvers can include polymers and copolymers of methacrylate, butadiene, olefins, or alkylated styrenes. Exemplary viscosity index improvers include, but are not limited to, polyisobutylene, copolymers of ethylene and propylene, hydrogenated block copolymers of styrene and isoprene, polyacrylates (e.g., polymers and/or copolymers of various chain length acrylates), and polymethacrylates (e.g., polymer and/or copolymers of various chain length alkyl methacrylates. Generally, the viscosity index improver can be used in an amount of from 0.01 wt. % to 6 wt. %, from 0.01 to 5 wt. %, or from 0.01 to 4 wt. % based upon the total weight of the composition.

Dispersants are additives utilized to maintain oxidation products (produced during use of the lubricant composition) in suspension in the lubricant compositions and/or functional fluid compositions to prevent the accumulation of debris that could score bearings, block lubricant pathways, prevent deposit formations, inhibit corrosive wear by neutralizing acidic products (e.g., combustion products), and other types of damage. Dispersants can be ash-containing or ashless in character. Dispersants can include, but are not limited to alkenylsuccinic acid or anhydride derivatives (e.g., succinimides, succinate esters, or succinate ester amides), phenates, Mannich-Base condensates (e.g., the condensation products of alkylphenols, amines and aldehydes), hydrocarbyl substituted amines, sulfonates, sulfurized phenates, salicylates, naphthenates, stearates, carbamates, thiocarbamates, and phosphorus derivatives in metallic and non-metallic versions. Suitable dispersants can contain a polar group attached to a relatively high molecular weight hydrocarbon chain where the polar group contains at least one element of nitrogen, oxygen, or phosphorus. Patents describing dispersants which can be utilized in the lubricant compositions and/or functional fluid compositions include, but are not limited to, U.S. Pat. Nos. 3,036,003; 3,087,936; 3,172,892; 3,200,107; 3,2145,707; 3,219,666; 3,254,025; 3,272,746; 3,275,554; 3,322,670; 3,329,658; 3,316,177; 3,438,757; 3,341,542; 3,413,347; 3,438,757; 3,444,170; 3,449,250; 3,454,555; 3,454,607; 3,519,565; 3,541,012; 3,565,804; 3,630,904; 3,632,511; 3,652,616; 3,666,730; 3,687,849; 3,697,574; 3,702,300; 3,703,536; 3,704,308; 3,725,277; 3,725,480; 3,726,882; 3,751,365; 3,755,433; 3,756,953; 3,787,374; 3,798,165; 3,803,039; 3,822,209; 3,948,800; 4,100,082; 4,234,435; 4,426,305; 4,454,059; 4,767,551; and 5,705,458, among others. Generally, dispersants can be used in an amount of about 0.1 wt. % to 20 wt. %, 0.1 wt. % to 15 wt. %, or from 0.1 wt. % to 8 wt. % based upon the total weight of the composition.

Detergents are additives utilized to maintain overall cleanliness by keeping sludge, carbon and deposit precursors suspended in the lubricant compositions and/or functional fluid compositions. Many detergents are chemically similar to dispersants. Detergents which can be utilized in the lubricant compositions and/or functional fluid compositions can include the alkali or alkaline earth metal of sulfates, sulfonates, phenates, carboxylates, phosphates, carboxylic acids, and salicylates. For example, suitable detergents can include, but are not limited to, the sulfonated alkylaromatic hydrocarbons, alkyl phenols, sulfurized alkyl phenols treated with an alkaline earth metal hydroxide or oxide (e.g., CaO, Ca(OH)$_2$, BaO, Ba(OH)$_2$, MgO, or Mg(OH)$_2$). Sulfonated alkylaromatic compounds can be prepared from sulfonic acids obtained by sulfonation of $C_9$ to $C_{80}$ (or $C_6$ to $C_{60}$) alkyl substituted aromatic hydrocarbons (having one or more than one alkyl groups) where the alkyl groups independently can be $C_3$ to $C_{70}$ alkyl groups and the aromatic portion can be benzene, toluene, xylene, naphthalene, or biphenyl. Alkyl phenol and/or sulfurized alkyl phenols can have one or more $C_4$ to $C_{30}$ alkyl groups. The detergents utilized in the lubricant compositions and/or functional fluid compositions can be neutral (i.e., produced using only enough alkali or alkaline earth compound to neutralize the sulfonated alkylaromatic compound, alkyl phenol, or sulfurized alkyl phenol) or can be overbased (i.e., produced using more alkali or alkaline earth compound than necessary to neutralize the sulfonated alkylaromatic compound, alkyl phenol, or sulfurized alkyl phenol). Generally, detergents can be used in an amount of 0.01 wt. % to 6.0 wt. %, 0.05 wt. % to 5.0 wt. %, or 0.1 to 4 wt. % based upon the total weight of the composition.

Defoamants (or anti-foam agents) are additives utilized to retard the formation of stable foam in the lubricant compositions and/or functional fluid compositions. Defoamants which can be utilized in the lubricant compositions and/or functional fluid compositions can include, but are not limited to, silicone compounds (e.g., polysiloxanes, such as silicon oil or polydimethyl siloxane, among others) and organic polymers. Defoamants can be utilized in conjunction with demulsifiers. Generally, the maximum amount of defoamants can be in an amount of 1 wt. %, 0.5 wt. % or 0.1 wt. % based upon the total weight of the composition.

Antioxidants are additives utilized to retard the oxidative degradation of the base oil(s) in the lubricant compositions and/or functional fluid compositions. Oxidative base oil degradation can produce deposits on metal surfaces, sludge, and/or increase the viscosity of the lubricant composition. Antioxidants which can be utilized in the lubricant compositions and/or functional fluid compositions include, but are not limited to, hindered phenols (ashless); neutral or basic metal salts of hindered phenols; hindered phenolic carboxylic acid (e.g., propionic acid) ester derivatives; bis-hindered phenols; alkylated and non-alkylated aromatic amines; sulfurized alkyl phenols; alkali or alkaline earth metal salts of sulfurized alkyl phenols; copper dihydrocarbyl thio or dithio-phosphates; copper salts of carboxylic acids (natural or synthetic); and copper salts of dithiacarbamates, dithiocarbamates, sulphonates, phenates, acetylacetonates and alkenyl succinic acids or anhydrides (neutral, basic or acidic). Patents describing antioxidants which can be utilized in the lubricant compositions and/or functional fluid compositions include, but are not limited to, U.S. Pat. Nos. 4,798,684 and 5,084,197. Generally, the antioxidants can be used in an amount of from 0.01 wt. % to 5 wt. %, from 0.01 to 2.5 wt. %, or from 0.01 wt. % to 1.5 wt. % based upon the total weight of the composition.

Anti-wear additives and extreme pressure additives are compounds utilized to reduce friction and wear of metal parts of the base oil(s) in the lubricant compositions and/or functional fluid compositions. Anti-wear additives and extreme pressure additives which can be utilized in the lubricant compositions and/or functional fluid compositions include, but are not limited to, metal alkylthiophosphates (e.g., a zinc alkylthiophosphonate having a $C_1$ to $C_{18}$ alkyl group), metal dialkyldithiophosphates (e.g., a zinc alkylthiophosphonate having $C_1$ to $C_{18}$ alkyl groups), sulfurized $C_3$ to $C_{30}$ aliphatic or arylaliphatic hydrocarbon olefins (acyclic or cyclic), polysulfides of thiophosphorus acids, polysulfides of thiophosphorus acid esters, phosphorothionyl disulfides, alkylthiocarbamoyl compounds (e.g., bis(dibutyl)thiocarbamoyl) in combination with a molybdenum compound (e.g., oxymolybdenum diisopropylphosphorodithioate sulfide) and phosphorus ester (e.g., dibutyl hydrogen phosphite, for example), thiocarbamates, thiocarbamate/molybdenum complexes (e.g., moly-sulfur alkyl dithiocarbamate trimer complexes), and/or glycerol ester (e.g., mono-, di-, and tri-oleates, mono-palmitates and mono-myristates). Patents describing anti-wear additives and/or extreme pressure additives which can be utilized in the lubricant compositions and/or functional fluid compositions include, but are not limited to, U.S. Pat. Nos. 2,443,264; 2,471,115; 2,526,497; 2,591,577; 3,770,854; 4,501,678; 4,941,984; 5,034,141; 5,034,142; 5,084,197; and 5,693,598. Generally, the total amount of anti-wear additives and extreme pressure additives used in the lubricant compositions and/or functional fluid compositions can be in an amount of from 0.01 wt. % to 6 wt. %, from 0.01 to 5 wt. %, or from 0.01 wt. % to 4 wt. % based upon the total weight of the composition.

Anti-rust additives are additives that protect lubricated metal surfaces against chemical attack by water or other contaminants. Anti-rust additives can function by 1) wetting the metal surface with a film of oil, 2) absorbing water into a water-in-oil emulsion, and/or 3) adhering to the metal to form a non-reactive surface, among other potential modes of function. Anti-rust additives which can be utilized in the lubricant compositions and/or functional fluid compositions include, but are not limited to, zinc dithiophosphates, metal phenolates, basic metal sulfonates, fatty acids, and amines. Generally, the amount of anti-rust additives used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Corrosion inhibitors are additives that reduce the degradation of metallic parts that are in contact with the lubricant compositions and/or functional fluid compositions. Corrosion inhibitors which can be utilized in the lubricant compositions and/or functional fluid compositions include, but are not limited to, thiadiazoles and triazoles. Patents describing corrosion inhibitors which can be utilized in the lubricant compositions and/or functional fluid compositions include, but are not limited to, U.S. Pat. Nos. 2,719,125; 2,719,126; and 3,087,932. Generally, the amount of corrosion inhibitors used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Pour point depressants are additives that reduce the minimum temperature at which the lubricant compositions and/or functional fluid compositions will flow or can be poured. Pour point depressants which can be utilized in the lubricant compositions and/or functional fluid compositions include, but are not limited to, polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Patents describing pour point depressants which can be utilized in the lubricant compositions and/or functional fluid compositions include, but are not limited to, U.S. Pat. Nos. 1,815,022; 2,015,748; 2,191,498; 2,387,501; 2,655,479; 2,666,746; 2,721,877; 2,721,878; and 3,250,715. Generally, the amount of pour point depressant used in the lubricant compositions and/or functional fluid compositions can be in an amount of from 0.01 wt. % to 5 wt. %, from 0.01 wt. % to 2.5 wt. %, or from 0.01 wt. % to 1.5 wt. % based upon the total weight of the composition.

Seal compatibility additives are compounds that swell elastomeric seals and can function by causing a chemical reaction in the fluid or a physical change in the seal elastomer. Seal compatibility additives which can be utilized in the lubricant compositions and/or functional fluid compositions include, but are not limited to, organic phosphates, aromatic esters, aromatic hydrocarbons, esters (e.g., butylbenzyl phthalate), and polybutenyl succinic anhydride. Generally, the amount of seal compatibility additive used in the lubricant composition and/or functional fluid compositions can be in an amount of from 0.01 wt. % to 3 wt. %, from 0.01 wt. % to 2.5 wt. %, or from 0.01 wt. % to 2 wt. % based upon the total weight of the composition.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

EXAMPLES

The following examples are set forth to provide a detailed description of how the methods claimed herein are evaluated, and are not intended to limit the scope of what the inventors regard as their invention.

Reagents

1-Decene (Chevron Phillips Chemical Company, LP) was used as obtained and contained approximately 40 ppm (by weight) water.

1-Dodecene (Chevron Phillips Chemical Company, LP) was used as obtained and contained approximately 40 ppm (by weight) water.

1-Tetradecene (Chevron Phillips Chemical Company, LP) was used as obtained and contained approximately 40 ppm (by weight) water.

1-Butanol was utilized as obtained.

$AlCl_3$ (Aldrich) was received as a fine powder, stored and handled in a nitrogen atmosphere, and was utilized as obtained.

$AlBr_3$ (Aldrich) was received as a fine powder, stored and handled in a nitrogen atmosphere, and was utilized as obtained.

SAPO-11 (Chevron—prepared according to method disclosed in U.S. Pat. No. 5,082,956).

Example 1

To a 1 liter round-bottomed flask, equipped with a magnetic stir bar operating at 700 rpm, was added 1-decene, 120 g (0.86 mol) under a static nitrogen atmosphere. The contents of the round-bottomed flask were heated to 94° C. at which time powdered $AlCl_3$, 0.6 g (4.5 mmol), was added to the round bottomed flask in a single portion. As the temperature rose to 130° C., additional 1-decene, 479 g (3.42 mol), was added to the round-bottomed flask over a period of 17 minutes to control the temperature of the reaction mixture. The temperature was then maintained at 130° C. for three hours using either a water cooling bath or a heating mantle. Gas chromatographic analysis (using a gas chromatograph equipped with a flame ionization detector) of the reaction mixture indicated that about 85% of the 1-decene had been converted into oligomers.

The reaction mixture was then quenched with an aqueous NaOH solution (20 mL of 4 wt. % NaOH). The organic phase was separated from the aqueous phase and then washed three times with water (120 mL). The organic phase was then filtered over 400-600 silica gel to give a clear filtrate. The filtrate was then distilled to remove decenes, dimers, and a small portion of the trimers. The resulting distilled oligomer product, containing trimers and higher oligomers, was then hydrogenated. The hydrogenated product had a 100° C. kinematic viscosity of about 6 cSt.

Example 2

To a 1 liter round-bottomed flask, equipped with a magnetic stir bar operating at 700 rpm, was added 1-decene, 166 g (1.19 mol) under a static nitrogen atmosphere. The contents of the round-bottomed flask were heated to 88° C. at which time powdered $AlBr_3$, 1.16 g (4.3 mmol), was added to the round bottomed flask in a single portion. As the temperature rose to 130° C., additional 1-decene, 419 g (2.99 mol), was added to the round-bottomed flask over a period of 30 minutes to control the temperature of the reaction mixture. The temperature was then maintained at 130° C. for three hours using either a water cooling bath or a heating mantle. Gas chromatographic analysis (using a gas chromatograph equipped with a flame ionization detector) of the reaction mixture indicated that about 84% of the 1-decene had been converted into oligomers.

The reaction mixture was then quenched with an aqueous NaOH solution (47 g of 1 wt. % NaOH). The organic phase was separated from the aqueous phase and then washed three times with water (120 mL). The organic phase was then filtered over 400-600 silica gel to give a clear filtrate. The filtrate was then distilled to remove decenes, dimers, and a small portion of the trimers. The resulting distilled oligomer product, containing trimers and higher oligomers, was then hydrogenated. The hydrogenated product had a 100° C. kinematic viscosity of about 6 cSt.

Both $AlCl_3$ and $AlBr_3$ appear to produce essentially the same product under similar conditions (1.1 mol % $AlX_3$ in relation to the quantity of 1-decene charged at a reaction temperature of 130° C. for 3 hours).

Example 3

To a 1 liter round-bottomed flask, equipped with a magnetic stir bar operating at 700 rpm, was added 1-decene, 146 g (1.04 mol) under a static nitrogen atmosphere. The contents of the round-bottomed flask were heated to 71° C. at which time powdered $AlCl_3$, 1.20 g (9.0 mmol), was added to the round bottomed flask in a single portion. An additional 1-decene, 436 g (3.11 mol), was added to the round-bottomed flask over a period of 3 minutes and the temperature of the reaction was maintained at 90° C. for 8 hours using either a water cooling bath or a heating mantle. Gas chromatographic analysis (using a gas chromatograph equipped with a flame ionization detector) of the reaction mixture indicated that about 68% of the 1-decene had been converted into oligomers.

The reaction mixture was then quenched with an aqueous NaOH solution (32 g of 3.5 wt. % NaOH). The organic phase was separated from the aqueous phase and then washed three times with water (120 mL). The organic phase was then filtered over 400-600 silica gel to give a clear filtrate. The filtrate was then distilled to remove decenes, dimers, and a small portion of the trimers. The resulting distilled oligomer product, containing trimers and higher oligomers, was then hydrogenated. The hydrogenated product had a 100° C. kinematic viscosity of about 11.5 cSt.

Example 4

To a 1 liter round-bottomed flask, equipped with a magnetic stir bar operating at 700 rpm, was added 1-decene, 568 g (4.05 mol), under a static nitrogen atmosphere. The contents of the round-bottomed flask were heated to 99° C. at which time powdered $AlBr_3$, 0.9 g (3.41 mmol), was added to the round bottomed flask in a single portion, and followed with additional 1-decene, 36 g (0.26 mol). The temperature of the reaction was maintained at 100° C. for five hours using either a water cooling bath or a heating mantle as needed. After one hour, gas chromatographic analysis (using a gas chromatograph equipped with a flame ionization detector) of the reaction mixture indicated that 55% of the 1-decene had converted to oligomers. After five hours gas chromatographic analysis of the reaction mixture indicated that about 71% of the 1-decene had been converted into oligomers and the oligomer product contained 16 wt. % dimer.

The reaction mixture was then quenched with 25.1 g water and 1.74 g aqueous NaOH solution (25 wt. % NaOH). The organic phase was separated from the aqueous phase and then washed three times with water (50 ml). The organic phase was then filtered over 400-600 silica gel to give a clear filtrate. The filtrate was then distilled to remove decenes, dimers, and a small portion of the trimers. The resulting oligomer product, containing trimers and higher oligomers, was then hydrogenated. The hydrogenated oligomer product had a 100° C. kinematic viscosity of 5.6 cSt, a 40° C. kinematic viscosity of 27.7 cSt, and a viscosity index of 145.

Example 5

To a 1 liter round-bottomed flask, equipped with a magnetic stir bar operating at 700 rpm, was added 1-decene, 605 g (4.31 mol), and 1-butanol, 0.19 g (2.56 mmol), under a static nitrogen atmosphere. The contents of the round-bottomed flask were heated to 95° C. at which time powdered $AlBr_3$, 0.92 g (3.45 mmol), was added to the round bottomed flask in a single portion, and followed with additional 1-decene, 10 g (0.07 mol). The temperature of the reaction was maintained at 100° C. for five hours using either a water cooling bath or a heating mantle as needed. After one hour, gas chromatographic analysis (using a gas chromatograph equipped with a flame ionization detector) of the reaction mixture indicated that 52% of the 1-decene had converted to oligomers. After five hours gas chromatographic analysis of the reaction mixture indicated that about 71% of the 1-decene had been converted into oligomers and the oligomer product contained 31 wt. % dimer.

The reaction mixture was then quenched with 25.1 g water and 1.74 g aqueous NaOH solution (25 wt. % NaOH). The organic phase was separated from the aqueous phase and then washed three times with water (50 ml). The organic phase was then filtered over 400-600 silica gel to give a clear filtrate. The filtrate was then distilled to remove decenes, dimers, and a small portion of the trimers. The resulting distilled oligomer product, containing trimers and higher oligomers, was then hydrogenated. The hydrogenated product had a 100° C. kinematic viscosity of 4.9 cSt, a 40° C. kinematic viscosity of 23.5 cSt, and a viscosity index of 138.

Organic Liquid Carrier Olefins

Several different olefin compositions and mixtures thereof were tested for their efficacy as organic liquid carrier olefin. The source and/or preparation of the base organic liquid carrier olefins are described herein. The olefin distributions of the organic liquid carrier olefin were determined using proton NMR.

$C_{20}$ Lewis acid dimer olefins were isolated by distillation from the oligomer product of Example 1. The isolated $C_{20}$ olefins contained approximately 12 mole % 1,2-disubstituted olefins, 0 mole % vinylidenes, 39 mole % trisubstituted olefins, and approximately 49 mole % tetrasubstituted olefins.

Isomerized 1-decene olefins were prepared by isomerizing 1-decene in the presence of a SAPO-11. The 1-decene and 10 wt. % SAPO-11 (based upon the weight of the 1-decene and SAPO-11) were placed in a round bottomed flask under a nitrogen atmosphere and stirred at 120° C. until a Fourier transform infrared analysis of the olefin showed that the alpha olefin content had decreased to below 5 mole % alpha olefin. The solution was then filtered to remove the SAPO-11 from the isomerized 1-decene. The isomerized 1-decene mixture comprised a nearly thermodynamic distribution of internal olefins having less than 5 mole % of 1-decene, based on the weight of the isomerized 1-decene mixture. The internal olefins of the isomerized 1-decene mixture contained approximately 93 mole % 1,2-disubstituted olefins, 0 mole % vinylidenes, 7 mole % trisubstituted olefins, and approximately 0 mole % tetrasubstituted olefins.

An isomerized 1-tetradecene mixture was prepared by isomerizing of 1-tetradecene in the presence of SAPO-11. The 1-tetradecene and 10 wt. % SAPO-11 (based upon the weight of the 1-tetradecene and SAPO-11) were placed in a round bottomed flask under a nitrogen atmosphere and stirred at 120° C. until a Fourier transform infrared analysis of the olefin showed that the alpha olefin content had decreased to below 5 mole % alpha olefin. The solution was then filtered to remove the SAPO-11 from the isomerized 1-tetradecene. The isomerized 1-tetradecene mixture comprised a nearly thermodynamic distribution of internal olefins having less than 5 mole % of 1-tetradecene, based on the weight of the isomerized 1-tetradecene mixture. The internal olefins to the isomerized 1-tetradecene mixture contained approximately 86 mole % 1,2-disubstituted olefins, 0 mole % vinylidenes, 14 mole % trisubstituted olefins, and approximately 0 mole % tetrasubstituted olefins. The disubstituted olefins of the isomerized 1-tetradecene olefin contained approximately 90 mole % linear 1,2-disubstituted olefins and approximately 10 mole % branched 1,2-disubstituted olefins.

A $C_{16}$ vinylidene-trisubstituted olefin mixture was obtained by distillation from the oligomer product produced from 1-octene oligomerization process using process as described in Example 6 of U.S. Pat. No. 8,536,391 using a catalyst system comprising a metallocene and chemically treated solid oxide activator. The $C_{16}$ vinylidene-trisubstituted olefin mixture contained approximately 6 mole % 1,2-disubstituted olefins, 32 mole % vinylidenes, 62 mole % trisubstituted olefins, and approximately 0 mole % tetrasubstituted olefins.

A $C_{16}$ trisubstituted olefin mixture was obtained by isomerizing a $C_{16}$ vinylidene-trisubstituted olefin mixture was obtained by distillation from the oligomer product produced from 1-octene oligomerization process using process as described in Example 6 of U.S. Pat. No. 8,536,391 using a catalyst system comprising a metallocene and chemically treated solid oxide activator. The $C_{16}$ vinylidene-trisubstituted olefin mixture was isomerized by contacting the $C_{16}$ vinylidene-trisubstituted olefin mixture with 20 wt. % dry Amberlyst® 15 for 16 minutes. The $C_{16}$ vinylidene-trisubstituted olefin mixture was then separated from the Amberlyst® 15 by filtration. The $C_{16}$ vinylidene-trisubstituted olefin mixture contained approximately 10 mole % 1,2-disubstituted olefins, 3 mole % vinylidenes, 87 mole % trisubstituted olefins, and approximately 0 mole % tetrasubstituted olefins.

A $C_{18}$ trisubstituted olefin mixture was obtained by the distillation of $C_{16}$-$C_{18}$-$C_{20}$ vinylidenes obtained from the tri-isobutyl aluminum dimerization of 1-octene and 1-decene. The $C_{18}$ trisubstituted olefin mixture contained approximately 6 mole % 1,2-disubstituted olefins, 94 mole % vinylidenes, 0 mole % trisubstituted olefins, and approximately 0 mole % tetrasubstituted olefins.

General Preparation of Aluminum Halide Catalyst Mixture

In a $N_2$ atmosphere drybox, a 20 mL vial containing an appropriate amount of $AlBr_3$ was charged with the appropriate amount of organic liquid carrier olefins (either a single organic liquid carrier olefin mixture described herein or a mixture of two organic liquid carrier olefin mixtures) to provide the desired liquid carrier olefin composition and desired catalyst mixture $AlBr_3$ molality. The catalyst mixture was allowed to stand at room temperature (approximately 22° C.). The olefin distributions of the organic liquid carrier and the $AlBr_3$ molalities are provided in Table 1.

General Oligomerization Test

In a $N_2$ atmosphere drybox, a 10 mL vial, equipped with a magnetic stir bar operating at 300 rpm, was charged with an appropriate amount of 1-dodecene and heated to 90° C. at which time the appropriate amount of organic liquid carrier to provide the desired $AlBr_3$:1-dodecene molar ratio. The 10 mL vial was maintained at 90° C. for two hours. Gas chromatographic analysis (using a gas chromatograph equipped with a flame ionization detector) of the reaction mixture was used to analyze the product and determine the amount of $C_{12}$ conversion which occurred. Table 1 provides the data on the liquid carrier olefin utilized, the olefin distribution of the liquid carrier olefin composition utilized, the $AlBr_3$ molality of the catalyst mixtures, how long the catalyst mixture was aged prior to its use in the 1-dodecene oligomerization, the $AlBr_3$ molarity utilized in the oligomerization, and the $C_{12}$ achieved for each 1-dodecene oligomerization run.

TABLE 1

$AlBr_3$ catalyst mixture using various olefin compositions mixtures and the use of the $AlBr_3$ catalyst mixtures for oligomerizing alpha olefins.

| Run # | Organic Liquid Carrier Olefin Identifier | Disubstituted Olefins (Mole %) | Vinylidenes (Mole %) | Trisubstituted Olefins (Mole %) | Tetrasubstituted Olefins (Mole %) | $AlBr_3$ (Molal) | Catalyst Mixture Age (Days) | $AlBr_3$:1-Dodecene Molar Ratio | 1-Dodecene Conversion (Mole %) |
|---|---|---|---|---|---|---|---|---|---|
| 1 | Lewis Acid Dimer Olefin | 12 | 0 | 39 | 49 | 0.88† | 4 | 5.3 × 10⁻³:1 | 0 |
| 2 | Isomerized | 93 | 0 | 7 | 0 | 1.25‡ | 1 | 6.4 × 10⁻³:1 | 81ᵃ |
| 3 | 1-Decene | | | | | | 2 | 3.4 × 10⁻³:1 | 84 |
| 4 | | | | | | | 7 | 3.1 × 10⁻³:1 | 83 |
| 5 | | | | | | | 29 | 3.1 × 10⁻³:1 | 82 |
| 6 | Isomerized 1-Tetradecene | 86 | 0 | 14 | 0 | 0.94‡ | 1 | 5.0 × 10⁻³:1 | 90 |
| 7 | $C_{16}$ Vinylidene- | 6 | 32 | 62 | 0 | 0.94 | 1 | 5.0 × 10⁻³:1 | 88 |
| 8 | Trisubstituted Olefin Mixture | | | | | | 1 | 1.0 × 10⁻²:1 | 93 |
| 9 | $C_{16}$ Trisubstituted | 10 | 3 | 87 | 0 | 0.94 | 1 | 5.0 × 10⁻³:1 | 92 |
| 10 | Olefin | | | | | | 7 | 5.0 × 10⁻³:1 | 90 |
| 11 | $C_{18}$ Vinylidene Olefin Mixture. | 6 | 94 | 0 | 0 | 0.42 | 1 | 2.4 × 10⁻³:1 | 0 |
| 12 | $C_{18}$ Vinylidene Olefin Mixture | 6 | 94 | 0 | 0 | 0.94 | 1 | 4.9 × 10⁻³:1 | 14 |
| 13 | Mixture of Lewis Acid Dimer Olefin and Isomerized 1-Decene | 12 | 0 | 39 | 49 | 0.42 | 5 | 4.9 × 10⁻³:1 | 2 |
| 14 | | 28 | 0 | 32 | 40 | 0.42 | 5 | 4.9 × 10⁻³:1 | 0 |
| 15 | | 46 | 0 | 24 | 30 | 0.42 | 5 | 4.9 × 10⁻³:1 | 0 |
| 16 | | 64 | 0 | 16 | 20 | 0.42 | 5 | 4.9 × 10⁻³:1 | 5 |
| 17 | | 82 | 0 | 8 | 10 | 0.42 | 5 | 4.9 × 10⁻³:1 | 0 |
| 18 | Mixture of Lewis Acid Dimer Olefin and Isomerized 1-Decene | 12 | 0 | 39 | 49 | 0.94 | 1 | 5.0 × 10⁻³:1 | 9 |
| 19 | | 28 | 0 | 32 | 40 | 0.94 | 1 | 5.0 × 10⁻³:1 | 6 |
| 20 | | 46 | 0 | 24 | 30 | 0.94 | 1 | 5.0 × 10⁻³:1 | 0 |
| 21 | | 64 | 0 | 16 | 20 | 0.94 | 1 | 5.0 × 10⁻³:1 | 24 |
| 22 | | 82 | 0 | 8 | 10 | 0.94 | 1 | 5.0 × 10⁻³:1 | 0 |
| 23 | Mixture of Lewis Acid Dimer Olefin and | 12 | 1 | 48 | 40 | 0.94 | 1 | 4.9 × 10⁻³:1 | 0 |
| 24 | | 11 | 1 | 58 | 30 | 1.00 | 1 | 5.0 × 10⁻³:1 | 0 |
| 25 | | 11 | 2 | 67 | 20 | 0.94 | 1 | 4.7 × 10⁻³:1 | 0 |

TABLE 1-continued

AlBr$_3$ catalyst mixture using various olefin compositions mixtures and the use of the AlBr$_3$ catalyst mixtures for oligomerizing alpha olefins.

| | | Catalyst Mixture Organic Liquid Carrier Olefins Composition and AlBr$_3$ Molality | | | | | Oligomerization Results | | |
|---|---|---|---|---|---|---|---|---|---|
| Run # | Organic Liquid Carrier Olefin Identifier | Disubstituted Olefins (Mole %) | Vinylidenes (Mole %) | Trisubstituted Olefins (Mole %) | Tetrasubstituted Olefins (Mole %) | AlBr$_3$ (Molal) | Catalyst Mixture Age (Days) | AlBr$_3$:1-Dodecene Molar Ratio | 1-Dodecene Conversion (Mole %) |
| 26 | C$_{16}$ Vinylidene-Trisubstituted Olefin Mixture | 10 | 2 | 77 | 10 | 0.94 | 1 | $5.3 \times 10^{-3}$:1 | 70 |

†After one hour dark globules were present in the catalyst system mixture.
‡The catalyst system mixture was clear and had a golden color.
$^a$GC analysis indicated that 70 mole % of the isomerized decene had been converted to oligomers and that C$_{10}$/C$_{12}$ mixed oligomer were present.

The oligomerization results show that 1,2-disubstituted olefins, trisubstituted olefins, or combination thereof are useful aluminum halide liquid carrier olefins and that the catalyst mixtures can be stored (for at least 29 days) without losing catalytic activity. Vinylidenes are tolerated in the aluminum halide liquid carrier olefins in moderate amounts (up to at least 32 mole %) in combination with 1,2-disubstituted olefins and/or trisubstituted olefins. Tetrasubstituted olefins are poorly tolerated in the aluminum halide liquid carrier olefins.

Example 6

The reaction system included a 500 mL stainless steel autoclave having an overhead magnetic stirrer, heating mantle, and internal cooling coils connected to a syringe pump and a metering pump. Product from the reactor was discharged through a research control valve to a product tank. The line between the autoclave and the product tank included a sample valve to enable the periodic collection of sample of the autoclave effluent.

A 0.5 molal catalyst mixture containing AlBr$_3$ (20 g, 0.75 mol) and isomerized 1-tetradecene (150 g) was charged to a 500-mL glass vessel equipped with magnetic stir bar in nitrogen filled drybox. The catalyst mixture charge vessel was sealed and the removed from the drybox. The catalyst mixture charge vessel was placed on a stirring plate and connected to the infusion side of a low pressure syringe pump and a low pressure nitrogen supply. Stirring and nitrogen purge was then initiated on the catalyst mixture charge vessel.

A 1-decene feed tank was charged with 1-decene (10 kg) under a N$_2$ atmosphere. The 1-decene feed tank was then sealed and connected to the infusion side of the metering pump and a low pressure nitrogen supply. A nitrogen purge was then initiated on the 1-decene feed tank. The 1-decene utilized contained approximately 40 ppm (by weight) water.

The 500 mL stainless steel autoclave equipped with an overhead magnetic stirrer was charged with approximately 250 mL 1-decene through the metering pump and the syringe pump was then charged with the catalyst mixture from the stirred and nitrogen purged catalyst mixture charge vessel. The temperature control system was set for 75° C. When the autoclave contents attained 75° C., the catalyst mixture was charged to the reactor through the syringe pump at a rate of 15 mL/h and 1-decene was charged to the reactor through the metering pump at a rate of 275 g/hour. Level controlled was utilized to maintain a one-half full reactor as observed on a connected sight-glass. After the initial reaction exotherm, the temperature control system of the autoclave was set to 100° C. and held at 100° C. for the remainder of the run. The reaction was sampled every 60 minutes using a sampling valve by purging the sampling valve for several minutes prior to taking a 20 mL sample of the reactor effluent. The 20 mL reactor effluent sample was then quenched with 100 mL aqueous NaOH solution (4 wt. % NaOH). The organic phase was separated from the aqueous phase and then washed three times with water (100 mL). The organic phase was again separated filtered via a syringe filter into a vial. The filtrate was analyzed by gas chromatography. Tabulated data for the sample is provided in Table 2.

TABLE 2

Analysis of Periodic Samples from Example 14.

| | | | Oligomer Product | | | |
|---|---|---|---|---|---|---|
| Reaction Time | Reaction Temperature | Conversion (wt. %) | C$_{20}$ (wt. %) | C$_{30}$ (wt. %) | >C$_{30}$ (wt. %) | Estimated 100° C. Kinematic Viscosity (cSt) |
| 1 hour | 90° C. | 6 | 33.3 | 33.3 | 33.3 | 7 |
| 2 hours | 100° C. | 32 | 31.3 | 43.8 | 12.5 | 5 |
| 3 hours | 100° C. | 49 | 30.6 | 36.7 | 12.2 | 6 |
| 4 hours | 100° C. | 47 | 21.3 | 38.3 | 19.2 | 6 |

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Additional Disclosure

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

Group A

Embodiment 1

A process comprising: contacting 1) a catalyst mixture comprising i) an aluminum trihalide and ii) an organic liquid carrier comprising first olefins, wherein the organic liquid carrier first olefins comprise at least 60 mole % 1,2-disubstituted olefins, trisubstituted olefins, or any combination thereof; and 2) a monomer comprising second olefins to form an oligomer product.

Embodiment 2

The process of embodiment 1, wherein the organic liquid carrier first olefins comprise less than 5 mole % alpha olefins.

Embodiment 3

The process of embodiment 1 or 2, wherein the organic liquid carrier first olefins comprise less than 20 mole % tetrasubstituted olefins, vinylidenes, or any combinations thereof.

Embodiment 4

The process of any of embodiments 1 to 3, wherein the organic liquid carrier first olefins comprise at least 75 mole % 1,2-disubstituted olefins and/or trisubstituted olefins, wherein the 1,2-disubstituted olefins and/or trisubstituted olefins comprise $C_6$ to $C_{24}$ disubstituted olefins, $C_6$ to $C_{24}$ trisubstituted olefins, or any combination thereof.

Embodiment 5

The process of any of embodiments 1 to 4, wherein the aluminum trihalide comprises aluminum trichloride, aluminum tribromide, or any combination thereof.

Embodiment 6

The process of any of embodiments 1 to 5, wherein the catalyst mixture has an aluminum trihalide to organic liquid carrier first olefins molal concentration ranging from 0.15 mole/kg to 4.0 mole/kg.

Embodiment 7

The process of any of embodiments 1 to 6, wherein the catalyst mixture further comprises a promoter.

Embodiment 8

The process of any of embodiments 1 to 6, wherein the catalyst mixture, the monomer, and a promoter are contacted to form an oligomer product.

Embodiment 9

The process of embodiment 7 or 8, wherein the promoter comprises water, an alcohol, a carboxylic acid, an ester, a ketone, an ether, a halogenated hydrocarbon, or any combination thereof.

Embodiment 10

The process of any of embodiments 1 to 9, wherein the catalyst mixture further comprises a metal halide, an alkyl metal halide, an alkyl metal compound, or any combination thereof or wherein the catalyst mixture, the monomer, and a metal halide, an alkyl metal halide, an alkyl metal compound, or any combination thereof are contacted to form an oligomer product.

Embodiment 11

The process of any of embodiments 1 to 10, wherein the aluminum trihalide and the monomer are contacted at a molar ratio ranging from $5 \times 10^{-8}:1$ to $1.1 \times 10^{-2}:1$.

Embodiment 12

The process of any of embodiments 1 to 11, wherein the monomer comprises $C_3$ to $C_{30}$ olefins.

Embodiment 13

The process of any of embodiments 1 to 12, wherein the monomer comprises alpha olefins.

Embodiment 14

The process of any of embodiments 1 to 13, wherein the monomer comprises 1-hexene, 1-octene, 1-decene, 1-dodecene, 1-tetradecene, or any combination thereof.

Embodiment 15

The process of any of embodiments 1 to 14, wherein the monomer comprises at least 50 mole % normal alpha olefins.

Embodiment 16

The process of any of embodiments 1 to 15, wherein the oligomer product is formed under oligomerization conditions comprising a temperature ranging from 0° C. to 200° C.

Embodiment 17

The process of any of embodiments 1 to 16, wherein the oligomer product is formed under oligomerization conditions comprising a substantial absence of an organic solvent.

Embodiment 18

The process of any of embodiments 1 to 17, wherein at least 50 mole % of the monomer is converted to the oligomer product.

Embodiment 19

The process of any of embodiments 1 to 18, further comprising contacting a reactor effluent with a catalyst deactivating agent.

Embodiment 20

The process of any of embodiments 1 to 19, further comprising separating at least a portion of the oligomer product from the monomer, to yield a separated oligomer product.

Embodiment 21

The oligomer product produced by the process of any of embodiments 1 to 20.

Embodiment 22

The process of any of embodiments 1 to 20, further comprising hydrogenating the separated oligomer product to form a polyalphaolefin.

Embodiment 23

The polyalphaolefin produced by the process of embodiment 22.

Embodiment 24

The polyalphaolefin of embodiment 23 having a 100° C. kinematic viscosity from 1.5 cSt to 50 cSt.

Embodiment 25

The polyalphaolefin of embodiment 23 or 24 having a minimum viscosity index of 100.

Embodiment 26

The polyalphaolefin of any of embodiments 23 to 25 having a pour point less than or equal to −20° C.

Embodiment 27

The polyalphaolefin of any of embodiments 23 to 26 having a maximum bromine number of 2.

Embodiment 28

A base oil comprising the polyalphaolefin of any of embodiments 23 to 27.

Embodiment 29

The base oil of embodiment 28 further comprising a Group I Base Oil, Group II Base Oil, Group III Base Oil, another Group IV Base Oil, a Group V Base Oil, or any combination thereof.

Embodiment 30

A lubricant or functional fluid comprising the base oil of embodiment 28 or 29.

Embodiment 31

The lubricant or functional fluid of embodiment 30 further comprising one or more additives selected from a viscosity index improver, a dispersant, a detergent, a friction modifier, a traction improving additive, a demulsifier, a defoamant, an antioxidant, an anti-wear additive, an extreme-pressure additive, an anti-rust additive, a corrosion inhibitor, a metal deactivators, an anti-seizure agent, a pour point depressant, a wax modifier, a seal compatibility agent, a friction modifier, a lubricity agent, an anti-staining agent, a chromophore, and a haze inhibitor.

Group B

A first embodiment, which is a process comprising:
contacting
1) a catalyst mixture comprising i) an aluminum trihalide and ii) an organic liquid carrier comprising first olefins, wherein the organic liquid carrier first olefins comprise at least 60 mole % 1,2-disubstituted olefins, trisubstituted olefins, or any combination thereof; and
2) a monomer comprising second olefins
to form an oligomer product.

A second embodiment, which is the process of the first embodiment, wherein the organic liquid carrier first olefins comprise less than 5 mole % alpha olefins.

A third embodiment, which is the process of any of the first through the second embodiments, wherein the organic liquid carrier first olefins comprise less than 20 mole % tetrasubstituted olefins, vinylidenes, or any combinations thereof.

A fourth embodiment, which is the process of any of the first through the third embodiments, wherein the organic liquid carrier first olefins comprise at least 75 mole % 1,2-disubstituted olefins and/or trisubstituted olefins, wherein the 1,2-disubstituted olefins and/or trisubstituted olefins comprise $C_6$ to $C_{24}$ disubstituted olefins, $C_6$ to $C_{24}$ trisubstituted olefins, or any combination thereof.

A fifth embodiment, which is the process of any of the first through the fourth embodiments, wherein the aluminum trihalide comprises aluminum trichloride, aluminum tribromide, or any combination thereof.

A sixth embodiment, which is the process of any of the first through the fifth embodiments, wherein the catalyst mixture has an aluminum trihalide to organic liquid carrier first olefins molal concentration ranging from 0.15 mole/kg to 4.0 mole/kg.

A seventh embodiment, which is the process of any of the first through the sixth embodiments, wherein the catalyst mixture further comprises a promoter.

An eighth embodiment, which is the process of any of the first through the seventh embodiments, wherein the catalyst mixture, the monomer, and a promoter are contacted to form an oligomer product.

A ninth embodiment, which is the process of the seventh or eighth embodiments, wherein the promoter comprises water, an alcohol, a carboxylic acid, an ester, a ketone, an ether, a halogenated hydrocarbon, or any combination thereof.

A tenth embodiment, which is the process of any of the first through the ninth embodiments, wherein the catalyst mixture further comprises a metal halide, an alkyl metal halide, an alkyl metal compound, or any combination thereof or wherein the catalyst mixture, the monomer, and a metal halide, an alkyl metal halide, an alkyl metal compound, or any combination thereof are contacted to form an oligomer product An eleventh embodiment, which is the process of any of the first through the tenth embodiments, wherein the aluminum trihalide and the monomer are contacted at a molar ratio ranging from $5 \times 10^{-8}$:1 to $1.1 \times 10^{-2}$:1.

A twelfth embodiment, which is the process of any of the first through eleventh embodiments, wherein the monomer comprises $C_3$ to $C_{30}$ olefins.

A thirteenth embodiment, which is the process of any of the first through twelfth embodiments, wherein the monomer comprises alpha olefins.

A fourteenth embodiment, which is the process of any of the first through the thirteenth embodiments, wherein the monomer comprises 1-hexene, 1-octene, 1-decene, 1-dodecene, 1-tetradecene, or any combination thereof.

A fifteenth embodiment, which is the process of any of the first through fourteenth embodiments, wherein the monomer comprises at least 50 mole % normal alpha olefins.

A sixteenth embodiment, which is the process of any of the first through fifteenth embodiments, wherein the oligomer product is formed under oligomerization conditions comprising a temperature ranging from 0° C. to 200° C.

A seventeenth embodiment, which is the process of any of the first through the sixteenth embodiments, wherein the oligomer product is formed under oligomerization conditions comprising a substantial absence of an organic solvent.

An eighteenth embodiment, which is the process of any of the first through the seventeenth embodiments, wherein at least 50 mole % of the monomer is converted to the oligomer product.

A nineteenth embodiment, which is the process of any of the first through the eighteenth embodiments, further comprising contacting a reactor effluent with a catalyst deactivating agent.

A twentieth embodiment, which is the process of any of the first through the nineteenth embodiments, further comprising separating at least a portion of the oligomer product from the monomer, to yield a separated oligomer product.

A twenty-first embodiment, which is the process of the twentieth embodiment, further comprising hydrogenating the separated oligomer product to form a polyalphaolefin.

A twenty-second embodiment, which is an oligomer product produced by the process comprising:
  contacting
    1) a catalyst mixture comprising i) an aluminum trihalide and ii) an organic liquid carrier comprising first olefins, wherein the organic liquid carrier olefins comprise at least 75 mole % 1,2-disubstituted olefins, trisubstituted olefins, or any combination thereof; and
    2) a monomer comprising second olefins
  to form an oligomer product.

A twenty-third embodiment, which is a polyalphaolefin produced by the process comprising:
  a) contacting
    1) a catalyst mixture comprising i) an aluminum trihalide and ii) an organic liquid carrier comprising first olefins, wherein the organic liquid carrier olefins comprises at least 75 mole % 1,2-disubstituted olefins, trisubstituted olefins, or any combination thereof; and
    2) a monomer comprising second olefins to form an oligomer product;
  b) separating at least a portion of the oligomer product from the monomer, to yield a separated oligomer product; and
  c) hydrogenating the separated oligomer product to form a polyalphaolefin.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process comprising:
  contacting
    1) a catalyst mixture comprising i) an aluminum trihalide and ii) an organic liquid carrier comprising first olefins, wherein the organic liquid carrier first olefins comprise at least 60 mole % 1,2-disubstituted olefins; and
    2) a monomer comprising second olefins
  to form an oligomer product.

2. The process of claim 1, wherein the organic liquid carrier first olefins comprise less than 5 mole % alpha olefins.

3. The process of claim 1, wherein the organic liquid carrier first olefins comprise less than 20 mole % tetrasubstituted olefins, vinylidenes, or any combinations thereof.

4. The process of claim 1, wherein the organic liquid carrier first olefins comprise at least 75 mole % 1,2-disubstituted olefins, wherein the 1,2-disubstituted olefins comprise $C_6$ to $C_{24}$ disubstituted olefins.

5. The process of claim 1, wherein the aluminum trihalide comprises aluminum trichloride, aluminum tribromide, or any combination thereof.

6. The process of claim 1, wherein the catalyst mixture has an aluminum trihalide to organic liquid carrier first olefins molal concentration ranging from 0.15 mole/kg to 4.0 mole/kg.

7. The process of claim 1, wherein the catalyst mixture further comprises a promoter.

8. The process of claim 1, wherein the catalyst mixture, the monomer, and a promoter are contacted to form an oligomer product.

9. The process of claim 7, wherein the promoter comprises water, an alcohol, a carboxylic acid, an ester, a ketone, an ether, a halogenated hydrocarbon, or any combination thereof.

10. The process of claim 1, wherein the catalyst mixture further comprises a metal halide, an alkyl metal halide, an alkyl metal compound, or any combination thereof or wherein the catalyst mixture, the monomer, and a metal halide, an alkyl metal halide, an alkyl metal compound, or any combination thereof are contacted to form the oligomer product; and wherein the metal halide and the aluminum trihalide are different.

11. The process of claim 1, wherein the aluminum trihalide and the monomer are contacted at a molar ratio ranging from $5 \times 10^{-8}$:1 to $1.1 \times 10^{-2}$:1.

12. The process of claim 1, wherein the monomer comprises $C_3$ to $C_{30}$ olefins.

13. The process of claim 1, wherein the monomer comprises alpha olefins.

14. The process of claim 1, wherein the monomer comprises 1-hexene, 1-octene, 1-decene, 1-dodecene, 1-tetradecene, or any combination thereof.

15. The process of claim 1, wherein the monomer comprises at least 50 mole % normal alpha olefins.

16. The process of claim 1, wherein the oligomer product is formed under oligomerization conditions comprising a temperature ranging from 0° C. to 200° C.

17. The process of claim 1, wherein the oligomer product is formed under oligomerization conditions comprising a substantial absence of an organic solvent.

18. The process of claim 1, wherein at least 50 mole % of the monomer is converted to the oligomer product.

19. The process of claim 1, further comprising contacting a reactor effluent with a catalyst deactivating agent.

20. The process of claim 1, further comprising separating at least a portion of the oligomer product from the monomer, to yield a separated oligomer product.

21. The process of claim 20, further comprising hydrogenating the separated oligomer product to form a polyalphaolefin.

* * * * *